(12) United States Patent
Sackett et al.

(10) Patent No.: US 8,052,687 B2
(45) Date of Patent: Nov. 8, 2011

(54) CALCAR PLANAR

(75) Inventors: Samuel G. Sackett, Fort Wayne, IN (US); Jonathan E. Carr, Warsaw, IN (US); David K. DeBoer, Franklin, TN (US)

(73) Assignee: DePuy Products, Inc., Warsaw, IN (US)

(*) Notice: Subject to any disclaimer, the term of this patent is extended or adjusted under 35 U.S.C. 154(b) by 758 days.

(21) Appl. No.: 11/529,886

(22) Filed: Sep. 29, 2006

(65) Prior Publication Data

US 2008/0161812 A1    Jul. 3, 2008

(51) Int. Cl.
  *A61B 17/00*   (2006.01)
  *A61B 17/58*   (2006.01)
  *A61F 5/00*    (2006.01)

(52) U.S. Cl. .................... 606/80; 606/87; 606/88
(58) Field of Classification Search ............. 606/79–80, 606/86 R, 85 R, 87–89
  See application file for complete search history.

(56) References Cited

U.S. PATENT DOCUMENTS

| | | | | |
|---|---|---|---|---|
| 4,023,572 A * | 5/1977 | Weigand et al. | | 606/81 |
| 4,306,550 A | 12/1981 | Forte | | |
| 4,790,852 A * | 12/1988 | Noiles | | 623/23.46 |
| 4,906,147 A * | 3/1990 | Friesinger et al. | | 409/232 |
| 5,047,033 A * | 9/1991 | Fallin | | 606/87 |
| 5,169,401 A | 12/1992 | Lester et al. | | |
| 5,342,366 A | 8/1994 | Whiteside et al. | | |
| 5,374,270 A * | 12/1994 | McGuire et al. | | 606/80 |
| 5,403,320 A * | 4/1995 | Luman et al. | | 606/89 |
| 5,468,243 A * | 11/1995 | Halpern | | 606/80 |
| 5,486,180 A * | 1/1996 | Dietz et al. | | 606/87 |
| 5,496,324 A * | 3/1996 | Barnes | | 606/79 |
| 5,534,005 A * | 7/1996 | Tokish et al. | | 606/80 |
| 5,540,694 A * | 7/1996 | DeCarlo et al. | | 606/80 |
| 5,569,255 A * | 10/1996 | Burke | | 606/79 |
| 5,607,431 A * | 3/1997 | Dudasik et al. | | 606/80 |
| 5,658,290 A * | 8/1997 | Lechot | | 606/80 |
| 5,957,925 A | 9/1999 | Cook et al. | | |
| 5,976,145 A * | 11/1999 | Kennefick, III | | 606/80 |
| 6,102,915 A * | 8/2000 | Bresler et al. | | 606/80 |
| 6,206,884 B1 | 3/2001 | Masini | | |
| 6,245,074 B1 * | 6/2001 | Allard et al. | | 606/80 |
| 6,264,647 B1 * | 7/2001 | Lechot | | 606/1 |
| 6,395,004 B1 * | 5/2002 | Dye et al. | | 606/86 R |
| 6,506,000 B2 * | 1/2003 | Lechot | | 407/35 |
| 6,702,822 B1 * | 3/2004 | Noiles et al. | | 606/89 |
| 6,780,190 B2 * | 8/2004 | Maroney | | 606/86 R |

(Continued)

FOREIGN PATENT DOCUMENTS

EP    0 548 485 A2    10/1992

*Primary Examiner* — Thomas C. Barrett
*Assistant Examiner* — Matthew Lawson
(74) *Attorney, Agent, or Firm* — Maginot, Moore & Beck

(57) ABSTRACT

A kit for removing calcar bone from a resected face around a bone canal of a long bone prepared to receive an orthopaedic implant is provided. The kit includes a trial for insertion into the bone canal of the long bone and a fixture. The fixture has a connector for connecting the fixture to the trial and a guide for guiding the calcar reamer. The kit also includes a calcar reamer for removing calcar bone from the resected face around the bone canal of the long bone. The reamer includes a feature for cooperation with the guide of the fixture. The kit further includes an implant for insertion into the bone canal of the long bone.

19 Claims, 24 Drawing Sheets

U.S. PATENT DOCUMENTS

| | | |
|---|---|---|
| 6,854,742 B2 * | 2/2005 | Salyer et al. .................... 279/93 |
| 6,890,336 B2 * | 5/2005 | Nordman ........................ 606/80 |
| 6,902,400 B1 * | 6/2005 | Roetzer ........................ 433/165 |
| 6,932,821 B2 | 8/2005 | White |
| 7,001,394 B2 * | 2/2006 | Gundlapalli et al. ........... 606/88 |
| 7,008,430 B2 * | 3/2006 | Dong et al. .................... 606/80 |
| 7,056,317 B2 * | 6/2006 | Lechot .............................. 606/1 |
| 7,090,677 B2 | 8/2006 | Fallin et al. |
| 7,104,996 B2 * | 9/2006 | Bonutti ....................... 606/86 R |
| 7,141,053 B2 * | 11/2006 | Rosa et al. .................. 606/86 R |
| 7,481,814 B1 * | 1/2009 | Metzger .......................... 606/87 |
| 7,935,118 B2 * | 5/2011 | Vendrely et al. ................ 606/87 |
| 2002/0099380 A1 * | 7/2002 | Salyer et al. ................... 606/80 |
| 2005/0085820 A1 * | 4/2005 | Collins et al. ................... 606/79 |
| 2005/0192588 A1 * | 9/2005 | Garcia ........................... 606/88 |
| 2005/0261694 A1 * | 11/2005 | Orton et al. ..................... 606/81 |
| 2006/0167460 A1 * | 7/2006 | Pinczewski et al. ............ 606/88 |
| 2007/0083208 A1 * | 4/2007 | Desarzens et al. .............. 606/80 |
| 2008/0177337 A1 * | 7/2008 | McGovern et al. ......... 606/86 R |

* cited by examiner

CALCAR PLANAR

TECHNICAL FIELD OF THE INVENTION

The present invention relates generally to the field of orthopaedics, and more particularly, to an implant for use in arthroplasty.

BACKGROUND OF THE INVENTION

Joint replacement surgery is quite common and it enables many individuals to function properly when they otherwise would not be possible to do so. Such patients of joint replacement surgery typically suffer from osteoarthritis or rheumatoid arthritis. Artificial joints usually comprise metallic, ceramic and/or plastic components that are fixed to existing bone.

Such joint replacement surgery is otherwise known as total joint arthroplasty. Total joint arthroplasty is a well-known surgical procedure by which a diseased and/or damaged joint is replaced with a prosthetic joint. In a typical total joint arthroplasty, the ends or distal portions of the bone adjacent the joint are resected or a portion of the distal part of the bone is removed and the artificial joint is secured thereto.

A hip prosthesis may be modular or consist of more than one component. Such modularity has many advantages including reduced inventory, greater selection of an optimum hip prosthesis, and to assist in performing less invasive surgical procedures with smaller skin incisions and less soft tissue disruption.

One such modular hip system includes a sleeve that is slideably fitted over distal stem for insertion into the femoral canal of a femur. Such a sleeve type modular system is sold by DePuy Orthopedics Inc., Warsaw, Ind., as the S-ROM hip system. The S-ROM hip system includes a distal stem, a sleeve which slideably fits over the distal stem, and a neck trial that fits to the distal stem. The modular implant of the S-ROM hip system includes a stem to which a sleeve may slideably fit.

During the S-ROM surgical procedure, a sleeve is positioned proximally in the reamed canal of a resected femur. Once the sleeve, in the form of a trial sleeve, is positioned into the canal at the resected surface of the femur, a distal stem trial is positioned in the canal through the sleeve until it is seated into its proper position. At that point, a neck trial is secured to the distal stem trial making the trial stem assembly. A trial head is placed on the trial neck and a trial reduction is performed. If the trial reduction is satisfactory, the trial assembly is removed from the canal of the femur and an implant sleeve is positioned in the canal and an implant stem is inserted through the opening of this sleeve into position.

During the S-Rom surgical procedure, the level of the horizontal neck cut and the placement of the sleeve are the main contributors to the leg length of the stem. The surgeon first makes the initial resection. If the initial horizontal neck resection is too high, of if the sleeve is positioned distally into the stem to obtain the optimum leg length, the surgeon is required to remove excess bone that is superior to the top edge of the trial sleeve. Removing this excess bone reduces the risk of bony impingement.

The current method for removing this excess bone is in the form of using an osteotome or a saw to remove the bone, orienting the saw or the osteotome along the top surface of the sleeve trial. The top surface of the sleeve trial may be scraped or defaced to the point that metal shavings are released into the patient and the size etchings on the sleeve trials may become illegible.

The present invention is directed to alleviate at least some of the aforementioned problems with the prior art.

SUMMARY OF THE INVENTION

The present invention is in the form of a calcar plane for the removal of excess bone that is superior to the S-ROM sleeve trial. The calcar planer may be connected directed to a rotary hand head device by way of a connection, for example, a Hudson connection. The rotary device may be either a power equipment or merely a T-handle. A post may thread onto the external threads from an S-ROM trial stem. A guide may be rotatably mounted to the post. The guide may be fitted into a circular groove in the post and be permitted to rotate 360° around the post to accommodate either a left hip prosthesis or a right hip prosthesis.

The instrument kit of the present invention may further include the calcar reamer which transverse along a slot formed in the guide. The slot permits the movement of calcar reamer in a vertical axis. The calcar reamer may include a protrusion or bulb in the middle of the cutting edge of the calcar reamer that may mate with a groove on the top of the trial sleeve to guide and control the cutting depth and direction of the cut of the excess bone superior to the S-ROM sleeve trial. The rod, guide, and planer are separate components and can be removed for cleaning, for example, for autoclaving.

According to one embodiment of the present invention, a kit for removing calcar bone from a resected face around a bone canal of a long bone prepared to receive an orthopaedic implant is provided. The kit includes a trial for insertion into the bone canal of the long bone and a fixture. The fixture has a connector for connecting the fixture to the trial and a guide for guiding the calcar reamer. The kit also includes a calcar reamer for removing calcar bone from the resected face around the bone canal of the long bone. The reamer includes a feature for cooperation with the guide of the fixture. The kit further includes an implant for insertion into the bone canal of the long bone.

According to another embodiment of the present invention, a kit for removing calcar bone from a resected face around a bone canal of a long bone prepared to receive an orthopaedic implant is provided. The kit includes a trial for insertion into the bone canal of the long bone and a fixture. The fixture has a connector for connecting said fixture to the trial and a guide. The kit also includes a calcar reamer for removing calcar bone from the resected face around the bone canal of the long bone. The reamer including a feature for cooperation with the guide of the fixture.

According to yet another embodiment of the present invention, an instrument assembly for use with an orthopaedic implant trial for removing calcar bone from a resected face around a bone canal of a long bone prepared to receive an orthopaedic implant is provided. The instrument assembly includes a fixture having a connector for connecting the fixture to the trial and a guide. The instrument assembly also includes a calcar reamer for removing calcar bone from the resected face around the bone canal of the long bone. The reamer has a feature for cooperation with the guide of the fixture.

According to another aspect of the instrument assembly of the present invention, the fixture is threadably connected to the trial.

According to another aspect of the instrument assembly of the present invention, the guide of the fixture defines a wall of the guide. The wall defines a slot for guiding the calcar reamer.

According to another aspect of the instrument assembly of the present invention, the fixture includes a column. The column defining a longitudinal axis and an external periphery of the column. The column is threadably attachable to the trial. The fixture also includes an arm extending outwardly from and connected to the external periphery of the column. The arm defines a wall of the arm. The wall defines a slot for guiding the calcar reamer.

According to another aspect of the instrument assembly of the present invention, the arm is rotatably connected to the column about the longitudinal axis of the column.

According to another aspect of the instrument assembly of the present invention, the feature of the reamer cooperates with the guide of the fixture. The feature includes a stop for limiting the movement of the reamer.

According to another aspect of the instrument assembly of the present invention, the fixture includes a column. The column defines a longitudinal axis and a cylindrical external periphery of the column. The column has an internal wall defining a cavity extending inwardly from a first end of the column. The internal wall is threaded to mate with an external fastener on the trial. The fixture also has an arm extending outwardly from and rigidly connected to the external periphery of the column. The arm defines a wall of the arm. The wall defines a slot for guiding the calcar reamer in a specified path.

According to another aspect of the instrument assembly of the present invention, the reamer includes a shaft portion defining a longitudinal axis and an external periphery of the reamer. The reamer also includes an end mill including a plurality of cutting edges extending from a first end of the shaft portion. The reamer also includes a connector extending from a second end of the shaft portion, opposed to the first end.

According to another aspect of the instrument assembly of the present invention, the end mill of the reamer includes a pilot extending outwardly from the end mill along the longitudinal axis of the shaft portion.

According to another aspect of the instrument assembly of the present invention, the shaft portion of the reamer includes a stop for cooperation with the guide of the fixture to limit the advancement of the end mill of the reamer.

According to a further embodiment of the present invention, there is provided a trial for use with a reamer having a central tip on a proximal portion thereof. The reamer is used for removing calcar bone from a resected face around a bone canal of a long bone prepared to receive an orthopaedic implant. The trial includes a body portion including a stem for insertion into the bone canal of the long bone. The stem defines a longitudinal axis of the body portion. The trial also includes a cone extending from the proximal end of the body portion. The cone has a proximal surface. The proximal surface is generally normal to the longitudinal axis of the body portion. The proximal surface defines a channel therein. The channel is adapted to mate with the central rim of the reamer.

According to a further embodiment of the present invention, there is provided a fixture for use with a orthopaedic implant trial and with a reamer for removing calcar bone from a resected face around a bone canal of a long bone prepared to receive an orthopaedic implant. The fixture includes a connecting portion for connecting the fixture to the orthopaedic implant trial and a guide portion. The guide portion cooperates with the calcar reamer for guiding the calcar reamer.

According to another aspect of the fixture of the present invention, the connecting portion of said fixture includes threads for connecting said fixture to the trial.

According to another aspect of the instrument assembly of the present invention, the guide of the fixture defines a wall of the guide. The wall defines a slot for guiding the calcar reamer.

According to another aspect of the instrument assembly of the present invention, the fixture also includes a column. The column defines a longitudinal axis and an external periphery of the column. The column is threadably attachable to the trial. The fixture also includes an arm extending outwardly from and connected to the external periphery of the column. The arm defines a wall of the arm. The wall defines a slot for guiding the calcar reamer.

According to another aspect of the instrument assembly of the present invention, the arm is rotatably connected to the column about the longitudinal axis of the column.

According to another aspect of the instrument assembly of the present invention, the fixture includes a column. The column defines a longitudinal axis and a cylindrical external periphery of the column. The column has an internal wall defining a cavity extending inwardly from a first end of the column. The internal wall is threaded to mate with an external fastener on the trial. The fixture also includes an arm extending outwardly from and rigidly connected to the external periphery of the column. The arm defines a wall of the arm. The wall defines a slot for guiding the calcar reamer in a specified path.

According to a further embodiment of the present invention, there is provided a method for performing joint arthroplasty. The method includes the steps of resecting a long bone to form a resected surface and removing bone from the canal of the long bone. The method also includes the steps of inserting a trial into the long bone, attaching a fixture to the trial and guiding a reamer with the fixture. The method also includes the steps of reaming a portion of the resected surface of the long bone with the reamer and implanting a stem implant into the canal of the long bone.

The technical advantages of the present invention include the ability of the instrument of the present invention to avoid damage to the top surface of the sleeve trial. For example, according to one aspect of the present invention, an instrument kit is provided for removing calcar bone from the resected face around a bone canal of a femur. The femur may be prepared to receive an orthopedic implant. The instrument kit includes a trial for insertion into the bone canal of the femur and a fixture including a connector for connecting the fixture to the trial, and a guide for guiding the calcar reamer. The calcar reamer is used to remove calcar bone from the resected face around the bone canal of the femur. The calcar reamer includes a feature for cooperation with the guide of the fixture. Thus, the present invention provides for an instrument kit that avoids damage to the top surface of the sleeve trial. The technical advantages of the present invention further include the reduction of risk of bony impingement. For example, according to another aspect of the present invention a method for performing joint arthroplasty is provided. The method includes the steps of resecting a femur to form a resected surface and removing bone from the canal of the femur. The method further includes the steps of inserting a trial to the long bone and determining if bony impingement will occur by having bone superior to the top face of the sleeve trial. If the potential of bony impingement is determined to be a possibility a fixture is attached to the trial and a reamer is guided with the fixture. The method further includes the step of reaming a portion of the resected surface of the femur with the reamer and implanting a neck trial. Thus, the present invention provides for the reduction of risk of bony impingement.

The technical advantages of the present invention further include the ability to precisely remove excess bone. For example, according to another aspect of the present invention, a fixture for removing calcar bone from the resected face around the bone canal of a femur is provided. The fixture includes a connector for connecting the fixture to the trial and a guide for guiding the calcar reamer. The calcar reamer includes a feature, for example, a bulb on the distal portion of the reamer. The bulb contacts the upper face of the sleeve and sets a precise distance between the reamer cutting surface and the top face of the sleeve such that the excess bone is precisely removed. Thus, the present invention provides for precisely removing excess bone from around the resected face of a femur.

The technical advantages of the present invention further include the ability to obtain accurate leg length of the stem. For example, according to yet another aspect of the present invention, a kit for removing calcar bone from a resected face around a bone canal of a femur is provided. The kit includes a fixture including a connector for connecting the fixture to the trial and a guide for guiding the calcar reamer. The trial including a sleeve is positioned in the canal of the femur and the trial and sleeve are precisely set to obtain an accurate leg length of the stem. The calcar reamer thus removes excess reamer around the resected face of the long bone such that proximal neck component of the trial stem accurately seats against the distal trial component such that an accurate trial assembly is used to perform a trial reduction. An implant for insertion in the long bone is then placed into the canal. Thus, the present invention provides for obtaining accurate leg length of the stem.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which.

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
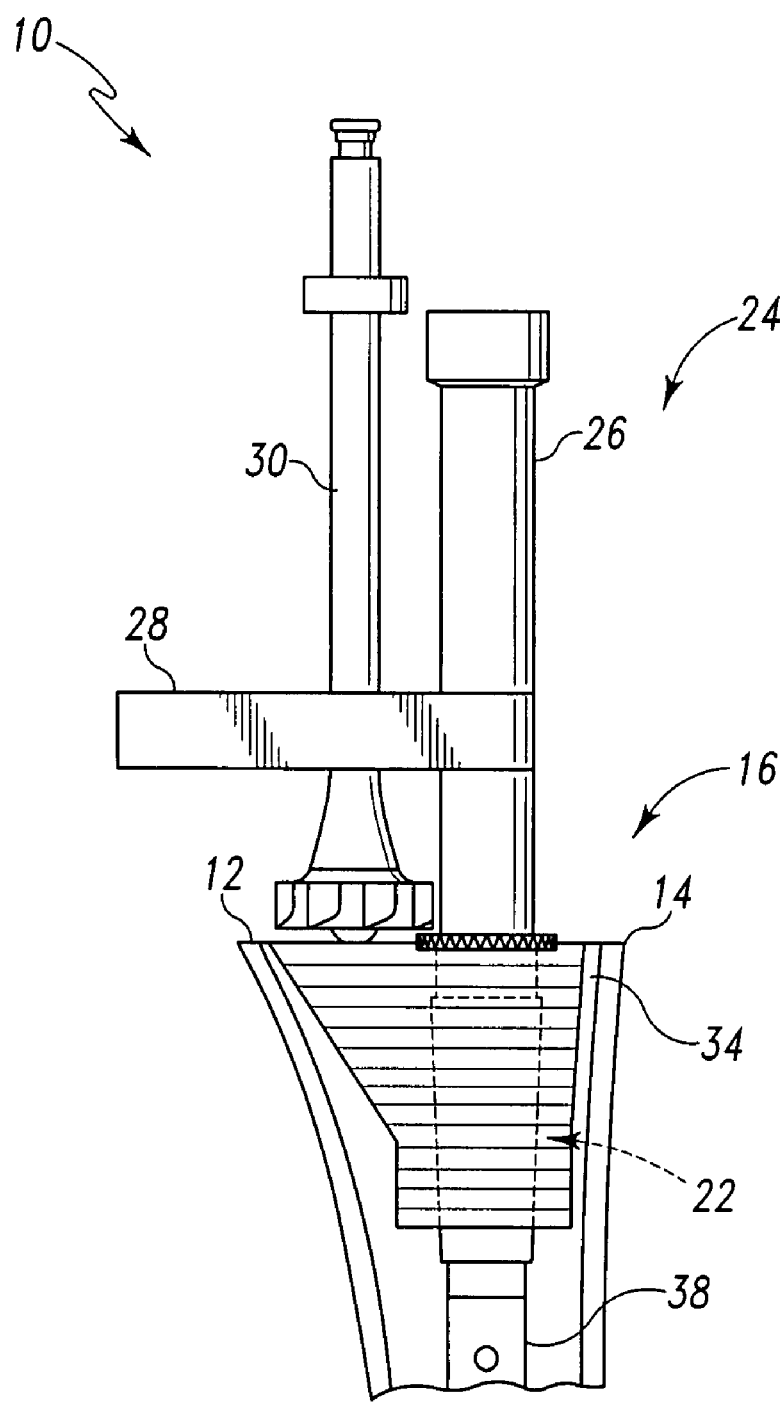
FIG. 1 is plan view of a kit including a trial, column, guide, and reamer is shown in cooperation with a femoral component of a hip prosthesis in accordance with an embodiment of the present invention.

According to the present invention and referring now to FIG. 1, a kit 10 for removing calcar bone 12 from a resected face 14 around a bone canal 16 of a long bone, for example, a femur 18 is shown. The long bone 18 is prepared to receive an orthopedic implant 20.

The kit 10 includes a trial 22 for insertion into the bone canal 16 of the femur 18. The kit 10 further includes a fixture 24 including a connector 26 for connecting the fixture 24 to the trial 22. The fixture 24 further includes a guide 28.

The kit 10 includes a calcar reamer 30 for reaming calcar bone 12 from the resected face 14 around the bone canal 16 of the femur 18. The calcar reamer 30 includes a feature 32 for cooperation with the guide 28 of the fixture 24.

Figure 2:
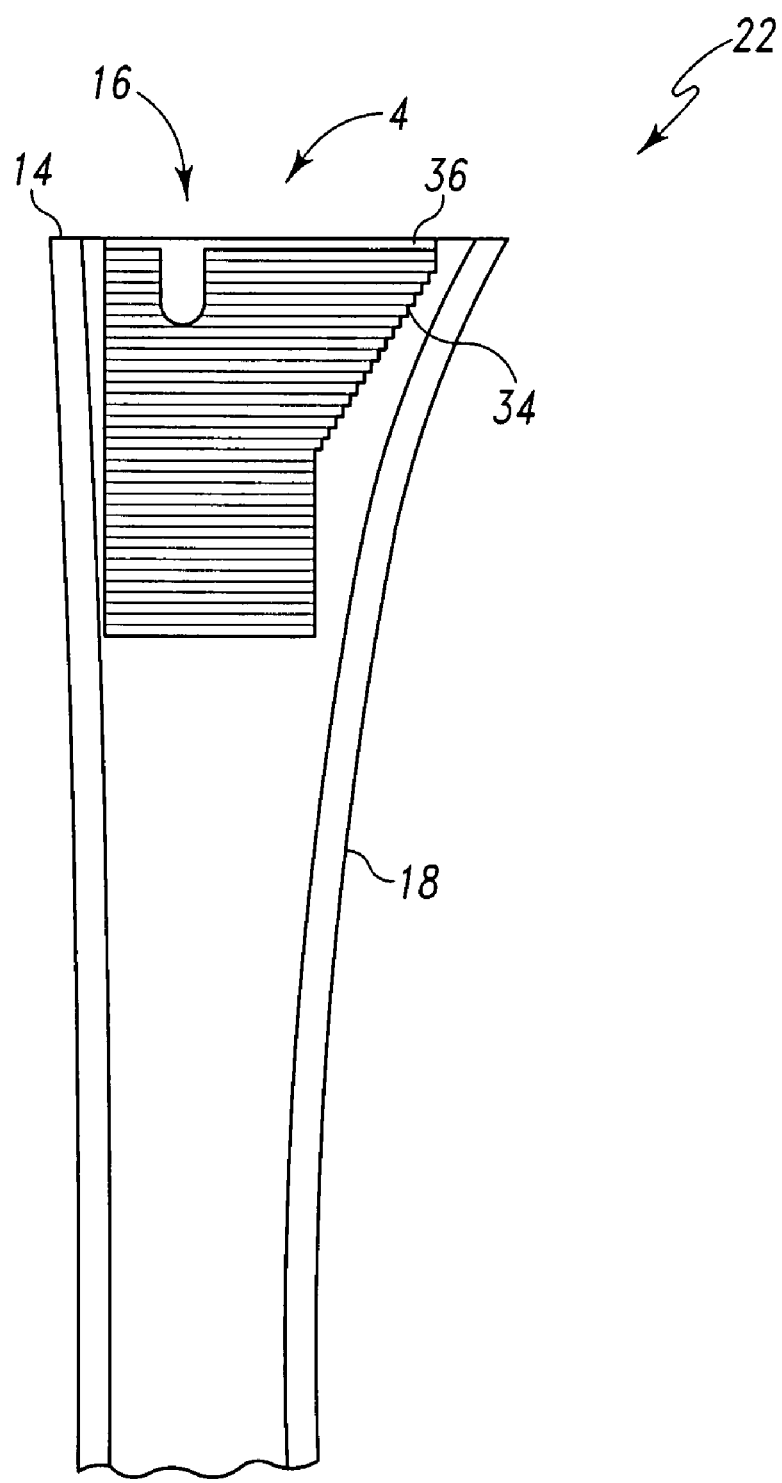
FIG. 2 is a plan view, partially in cross section, of a femur that may use kit of the present invention.

Referring now to FIG. 2, the femur 18 is shown in greater detail, with sleeve 34 of the trial 22 shown in position in cavity 4 formed in canal 6 of the femur 18. The sleeve 34 is positioned in the cavity 4. As shown in FIG. 2, the sleeve 34 includes planer proximal face 36 which may, as is shown in FIG. 2, lie below resected face 14 of the femur 18. The portion of the femur 18 lying above resected face 36 of the sleeve 34 may cause interference during the assembly of the proximal neck portion 22 of the trial when the proximal neck portion 22 of the trial is positioned adjacent the resected face 14 of the femur 18.

Figure 3:
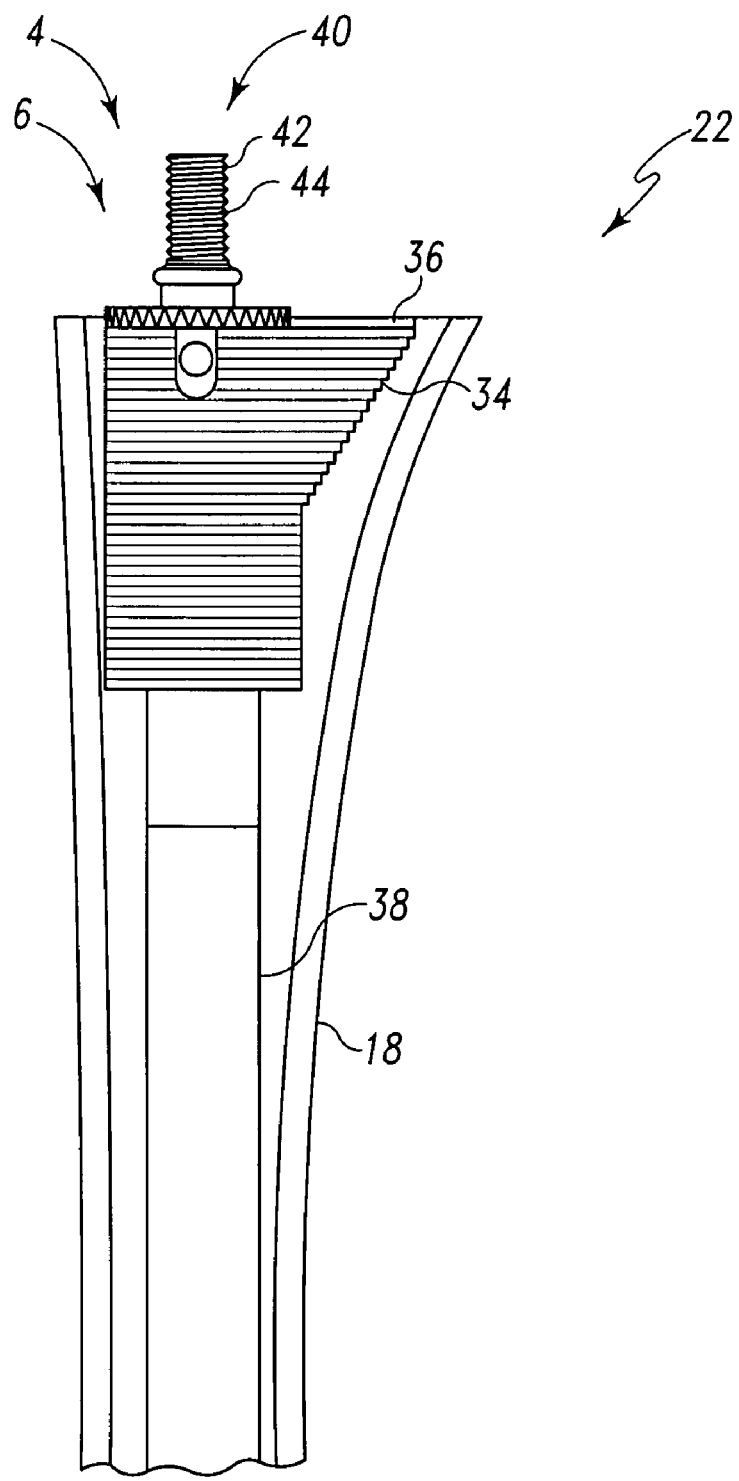
FIG. 3 is a plan view, partially in cross section, showing the distal stem of the trial of the kit of FIG. 1 in position in the femur of FIG. 2

Referring now to FIG. 3, the femur 18 is shown with distal stem 38 of the trial 22 inserted through longitudinal opening 40 of the sleeve 34 and into canal 6 formed in cavity 4 of the femur 18. The distal stem 38 includes a threaded portion 42 including external threads 44 for cooperation with fixture 24 of the kit 10.

Figure 4:
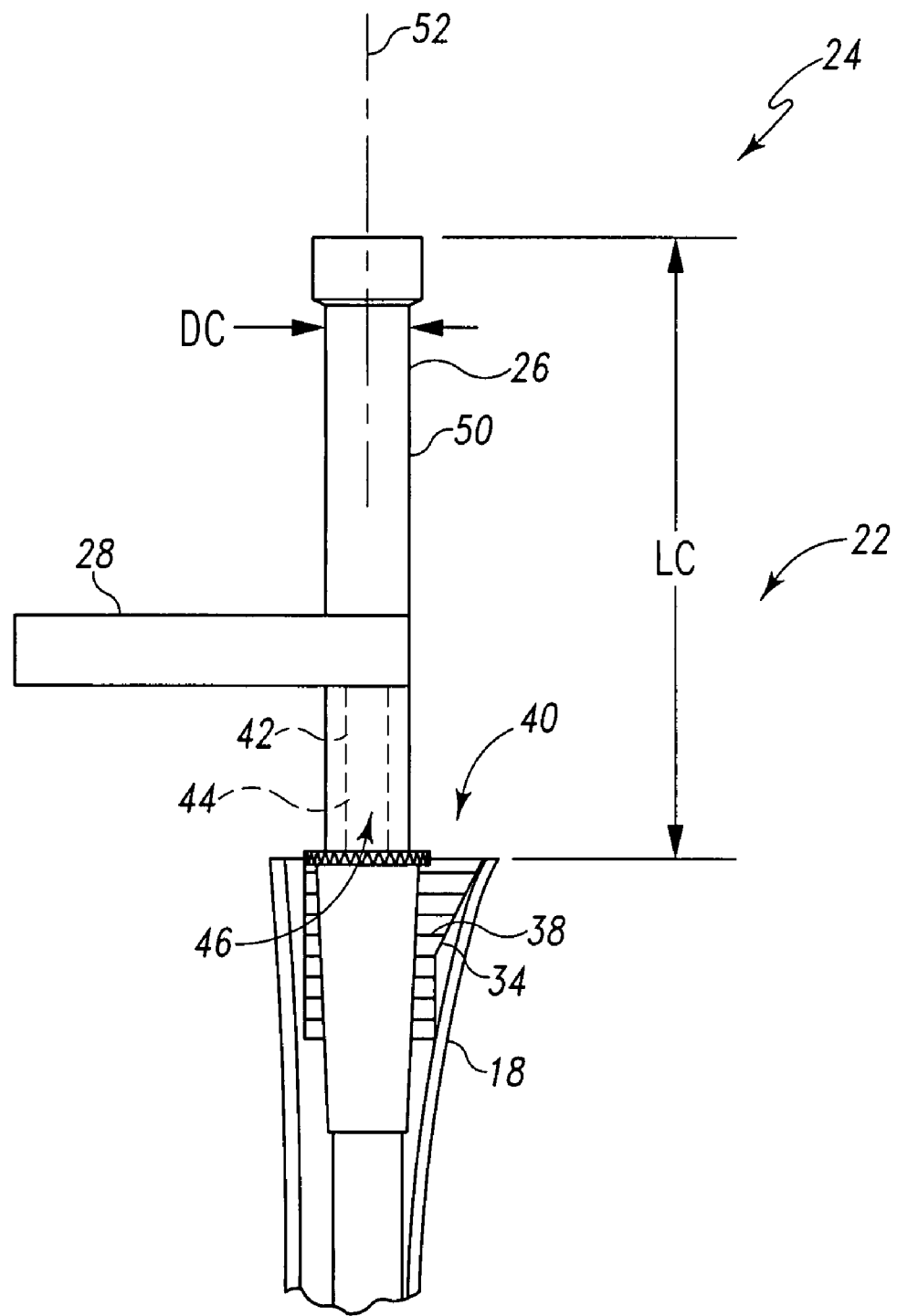
FIG. 4 is a plan view, partially in cross section, showing the distal stem of the trial, the column, and the guide of the kit of FIG. 1 in position in the femur of FIG.

Referring now to FIG. 4, the fixture 24 is mounted on distal stem 38 of the trial 22. The fixture 24 includes the connector 26 as well as guide 28. The fixture 24 may be preassembled with the guide 28 affixed to the connector 26 when installing the fixture 24 to the distal stem 38. Alternatively, the connector 26 may be installed to the distal stem and then the guide may be fastened to the connector 26. The connector 26 includes a distal longitudinal opening 46 which defines internal threads 48 which mate with the external threads 44 of the threaded stem 42 of the distal stem 38. It should be appreciated that the connector 26 may be secured to the distal stem 38 in any suitable fashion, for example, by a slip-fit, a press-fit, a bayonet connection, or any other type of connection.

The connector 26, as shown in FIG. 4, for simplicity is generally cylindrical and defined by a diameter DC and a length LC. The connector 26, thus, is generally in the shape of a column.

The guide 28, as shown in FIG. 4, is rotatably connected to the connector 26, or column 26, of the fixture 24 in any suitable manner and may define a guide rotational center line 50 which is concentric with longitudinal center line 52 of the column 26. While the column 26 may be integral, as shown in FIG. 4, the column 26 is module such that the column 26 may be separated to receive the guide 28.

Figure 5:
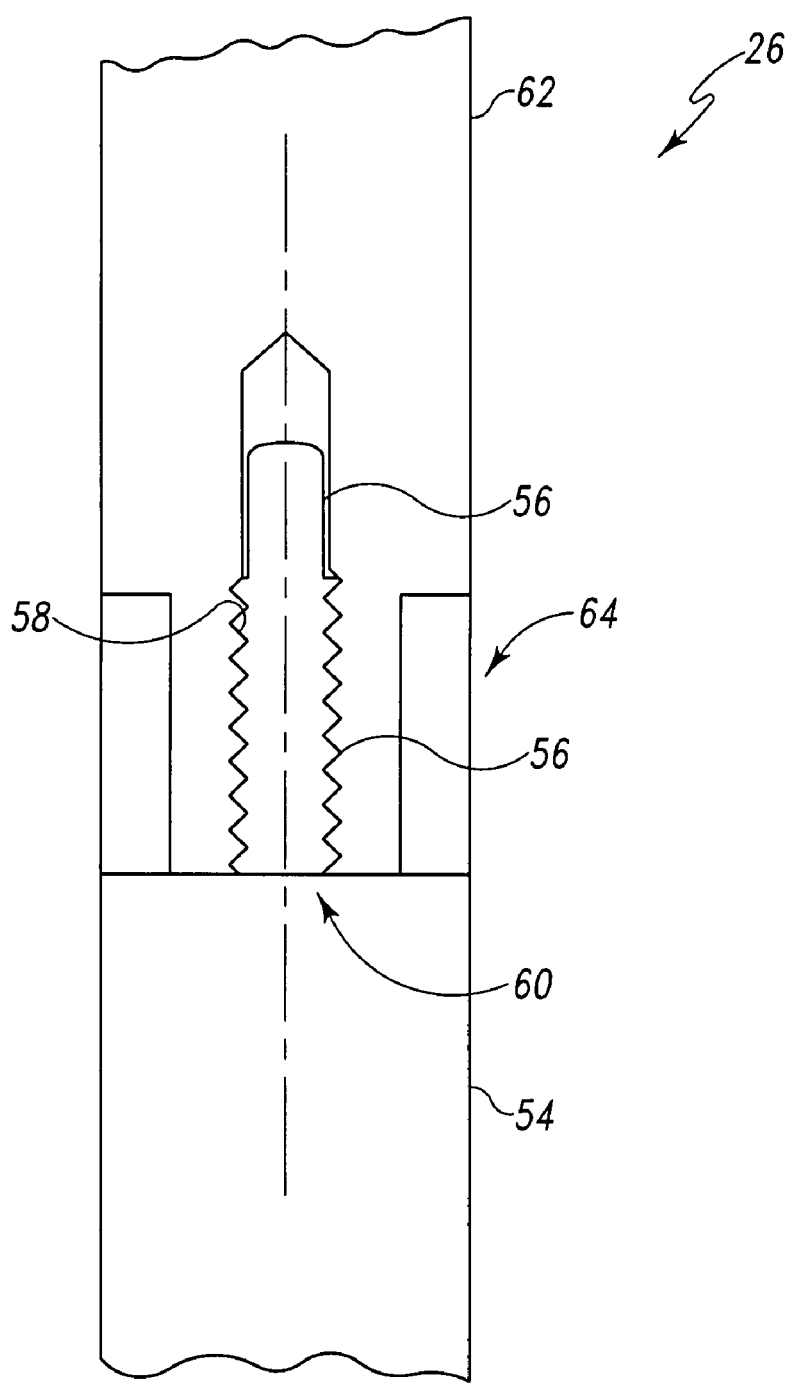
FIG. 5 is a partial plan view, partially in cross section, showing the connection of the column to the trial for the kit of FIG. 1.

For example and as shown in FIG. 5, the column 26 includes a lower portion 54 which includes the longitudinal opening 46 and internal threads 48. The lower portion 54 includes a threaded stem 56 which mates with internal threads 58 formed on longitudinal opening 60 of upper component 62. The upper component 62 includes a circumferential recess 64 which mates with first end 66 of the guide 28. The first end 66 of the guide 28 includes a cylindrical opening 68 which is fitted to the recess 64 of the upper component 62 of the column 26. The recess 64 and the longitudinal opening 68 of the guide 28 are fitted such that the guide 28 may rotate around longitudinal axis 52 of the column 26.

Figure 6:
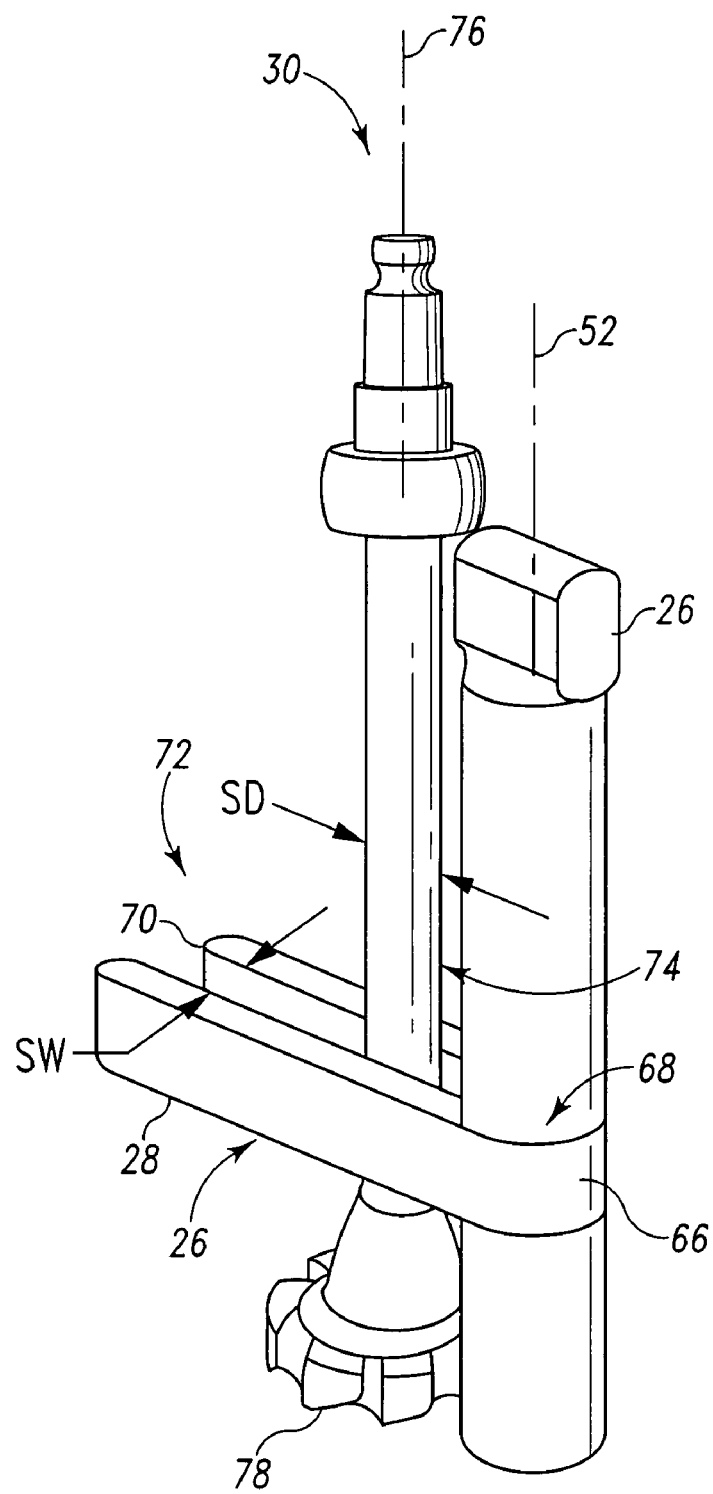
FIG. 6 is a perspective view of the kit of FIG. 1.

Referring now to FIG. 6, the guide 28 is shown in greater detail. The guide 28 includes an internal wall 70 defining a longitudinal slot 72 for receiving the calcar reamer 30. The slot 72 has a width SW which is sized to fit shaft diameter SD of the shaft 74 of the calcar reamer 30. As shown in FIG. 6, the calcar reamer 30 includes a longitudinal axis 76 about which the calcar reamer rotates. The longitudinal axis 76 may rotate around longitudinal axis 52 of the column 26 and the longitudinal axis 76 of the reamer 30 may move outwardly along the slot 72 to have the cutting edge 78 of the calcar reamer 30 remove the calcar bone from the resected face 14 of the femur 18, according to the present invention.

Figures 7, 7A:
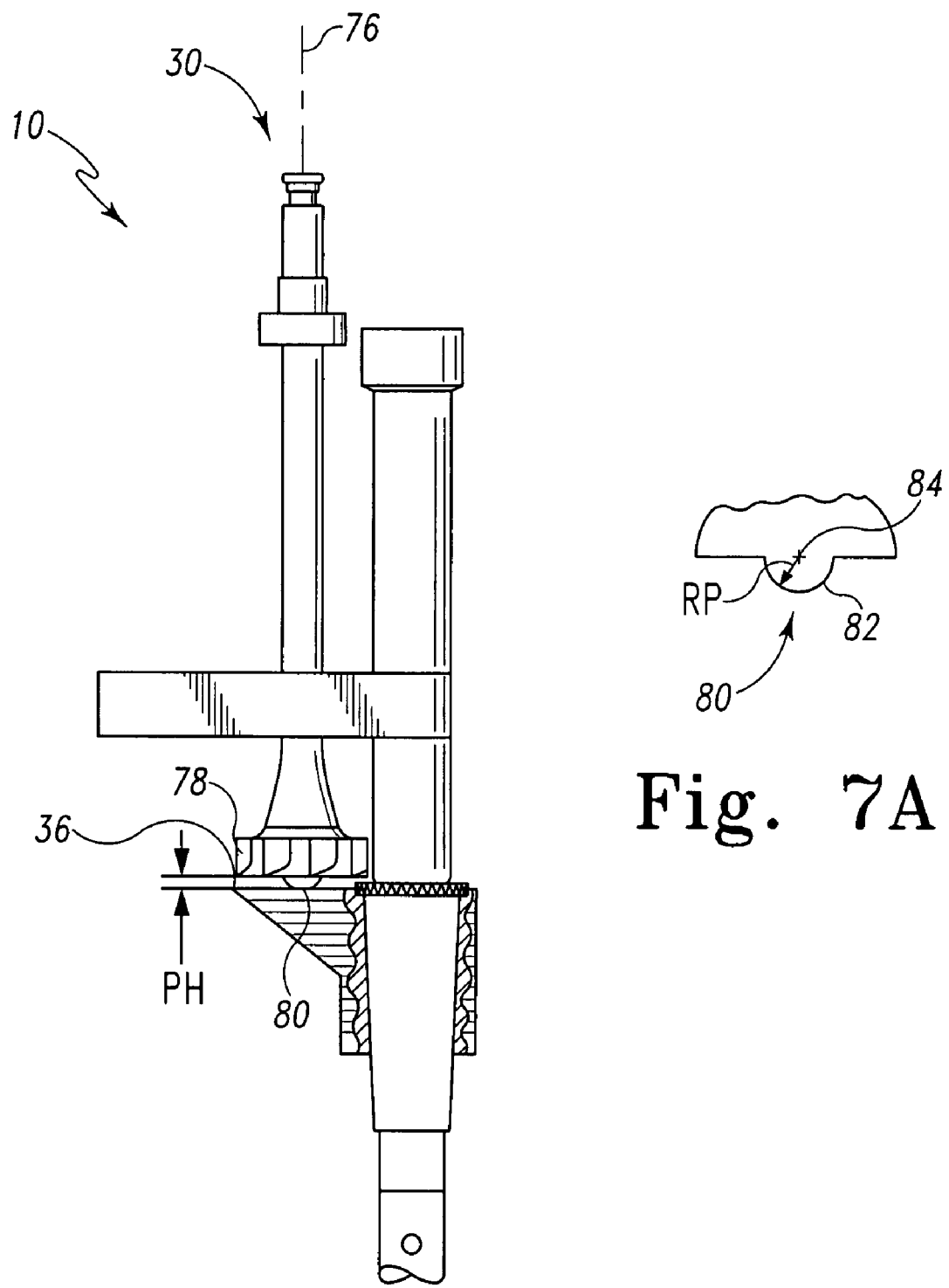
FIG. 7 is a partial plan view of the kit of FIG. 1, showing the trial, column, guide, and reamer in greater detail.
FIG. 7A is a partial plan view of the reamer of the kit of FIG. 1, showing the pilot of the reamer in greater detail.
Figure 8:
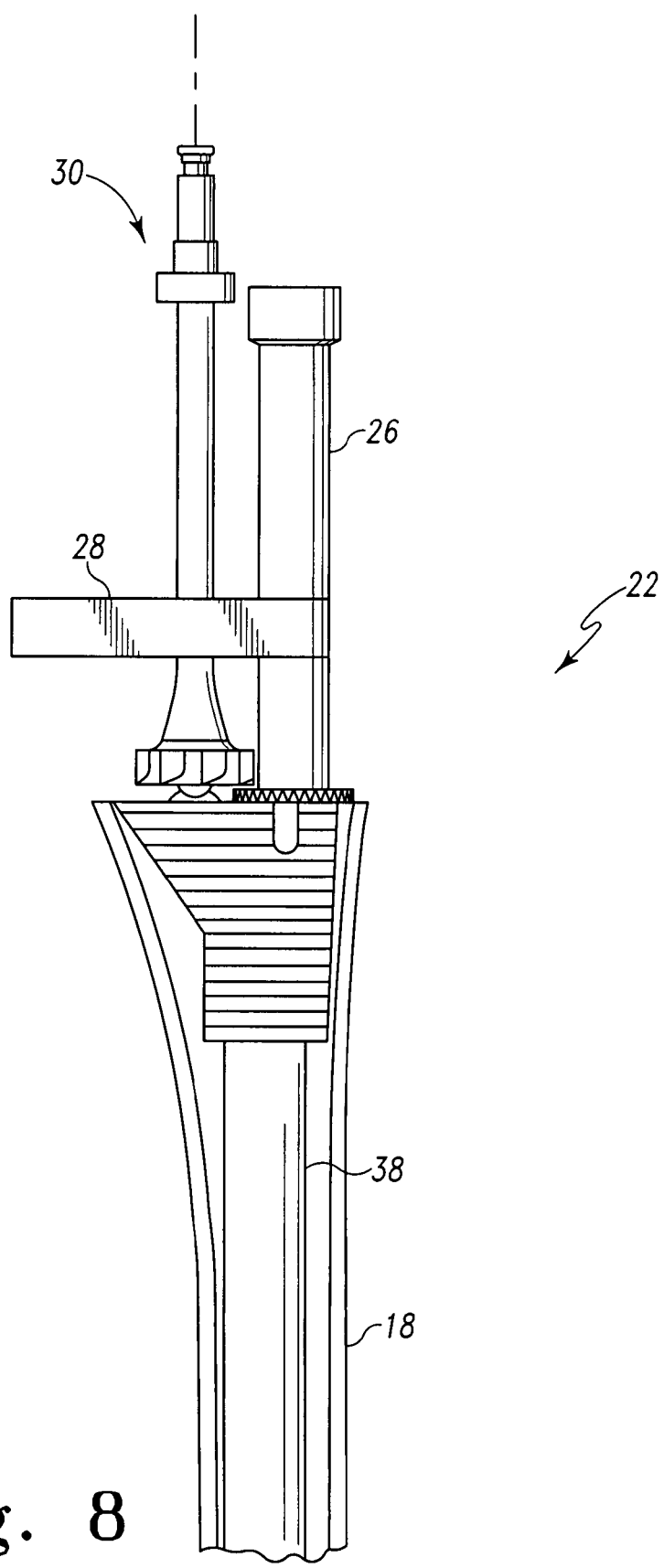
FIG. 8 is a plan view of the kit of FIG. 1, showing the trial, column, and guide and with the reamer in position in the femur.

Referring now to FIGS. 7, 7A and 8, the cutting edge 78 of the reamer 30 includes a protrusion, or pilot, 80 which extends outwardly and central along longitudinal axis 76 of the reamer 30. The pilot 80 has a pilot height PH. The pilot 80 may have a bulb shape or arcuate periphery 82.

Referring now to FIG. 7A, the periphery 82 may be spherical and may be defined by radius RP extending from origin 84.

Referring now to FIG. 7, the pilot 80 engages upper surface, or face, 36 of the sleeve 34 so that the cutting edge 78 of the reamer 30 prepares the proper amount of calcar bone from the resected face 14 of the femur 18.

Figure 9:
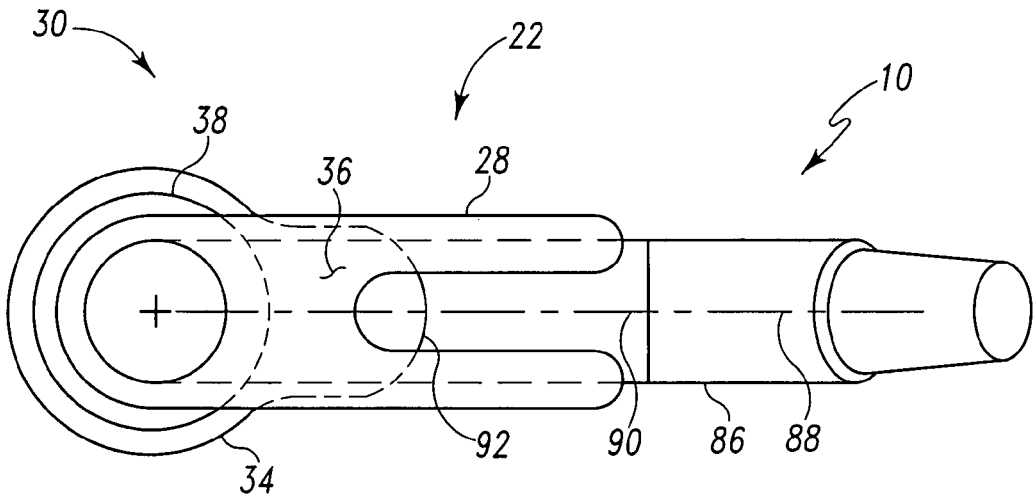
FIG. 9 is a top view of the trial of the kit of FIG. 1, showing the sleeve and the neck trial in radial alignment with each other.

Referring now to FIG. 9, the distal stem 38 receives neck trial 86. The neck trial 86, the distal stem 38, and the resected face 14 of femur 18 need to be designed and prepared so that the neck trial 86 does not impinge upon calcar bone 12 on resected face 14 of the femur 18. Thus, the calcar reamer 30 needs to be positioned such that the calcar reamer 30 removes the calcar bone 12 from the resected face 14 in alignment with the neck trial 86.

As shown in FIG. 9, the neck trial 86 defines a neck trial center line 88. It should be appreciated that the neck trial center line 88 of the neck trial 86 may be in alignment, or coincident, with spout center line 90 of the spout 92 of the sleeve 34. When the reamer 30 is utilized to remove the calcar bone from the resected face with the neck trial 88 in alignment with the spout 92 of the sleeve 34, it should be appreciated that the calcar reamer 30 may be utilized in its position over the top face 36 of the sleeve 34.

Figure 10:
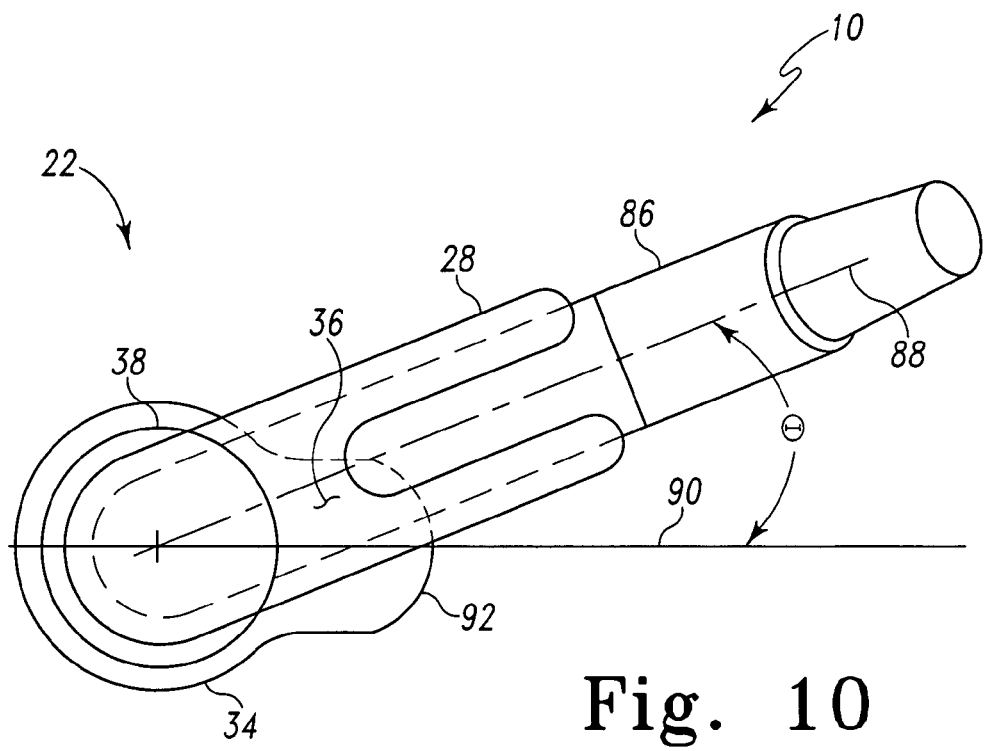
FIG. 10 is a top view of the trial of the kit of FIG. 1, showing the sleeve and the neck trial out of radial alignment with each other.

It should be appreciated that the neck trial 86 needs to be positioned in its proper anatomical location and may not be aligned with the spout 92. The spout 92 that should be aligned to fill or to accommodate a void or feature in the femur 18. For example and as shown in FIG. 10, the neck trial center line 88 of neck trial 86 may be offset an angle θ from spout center line 90 of spout 92. Since the top face 36 of the sleeve 34 is not in alignment with the neck trial 88, top face 36 of the sleeve 34 may not be used as a depth guide for the proper positioning of the calcar reamer 30 when reaming the calcar bone 12 from the resected face 14 of the femur 18.

Figure 11:
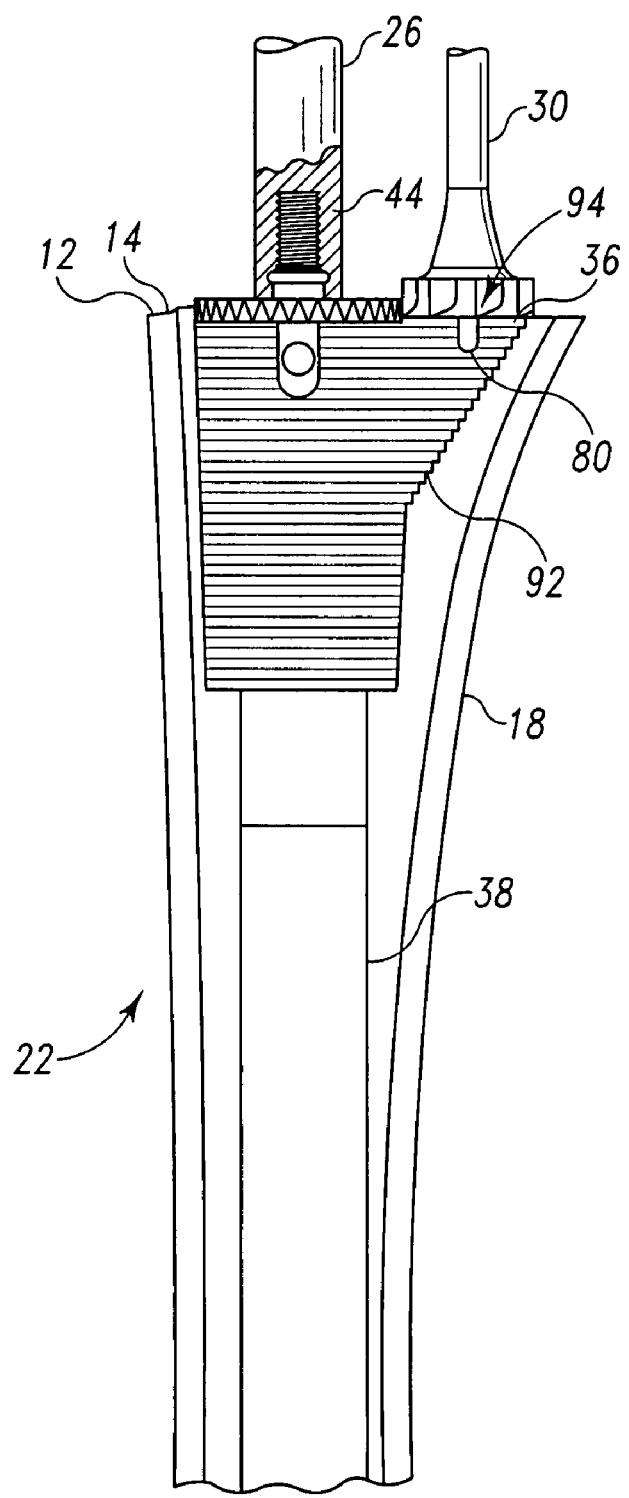
FIG. 11 is a partial plan view, partially in cross section, of the trial of the kit of FIG. 1, showing the channel in the top of the sleeve according to an aspect of the present invention.

If the spout 92 is in alignment with the neck trial 86, the top face of the sleeve may be smooth and the pilot of the reamer of the present invention may be translated along the flat surface of the sleeve to remove calcar bone. However, it should be appreciated that to steady the reamer and to avoid wear on the face of the sleeve when the spout 92 is in alignment with the neck trial 86, the sleeve 34 may include a feature on the face in the form of, for example, channel 94. As shown in FIG. 11, the channel 94 extends inwardly from top face 36 of the spout 92 of the sleeve 34 of the trial 22.

Figure 12:
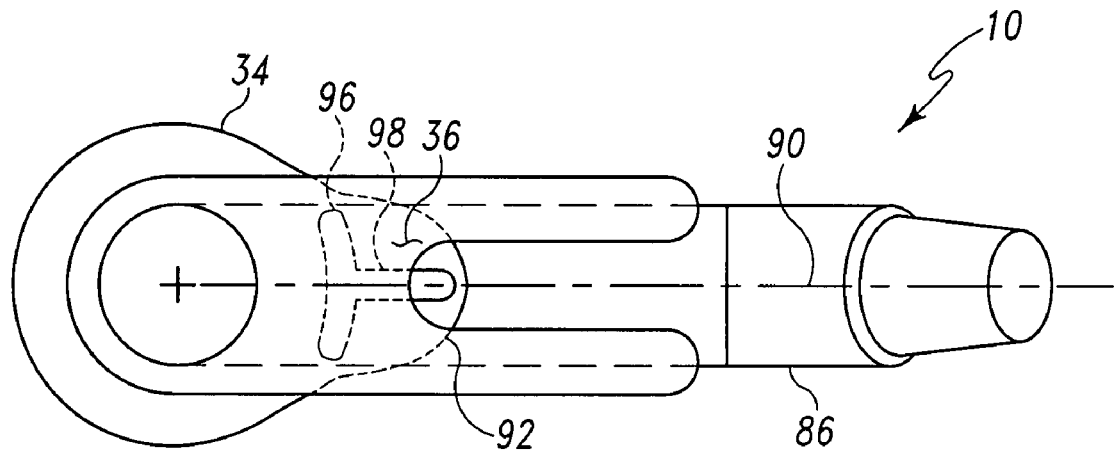
FIG. 12 is an enlarged partial top view of the trial of the kit of FIG. 1, showing the channel in the top of the sleeve.

Referring now to FIG. 12, the channel 94 may include a circumferential portion 96 and a radial portion 98 extending centrally and outwardly from the circumferential portion 96 of the channel 94. As shown in FIG. 12, the channel 94 may be centrally located on the top face 36.

Figure 13:
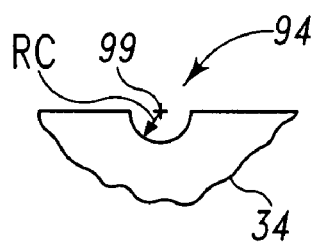
FIG. 13 is a partial plan view, partially in cross section, of the trial of the kit of FIG. 1, showing the channel in the top of the sleeve in greater detail.

Referring now to FIG. 13, the channel 94 may have any suitable shape and may, for simplicity, have a shape similar to that of the pilot 80 of the calcar reamer 30. For example, the channel 94 may be defined by radius RC extending from origin 99.

Figure 14:
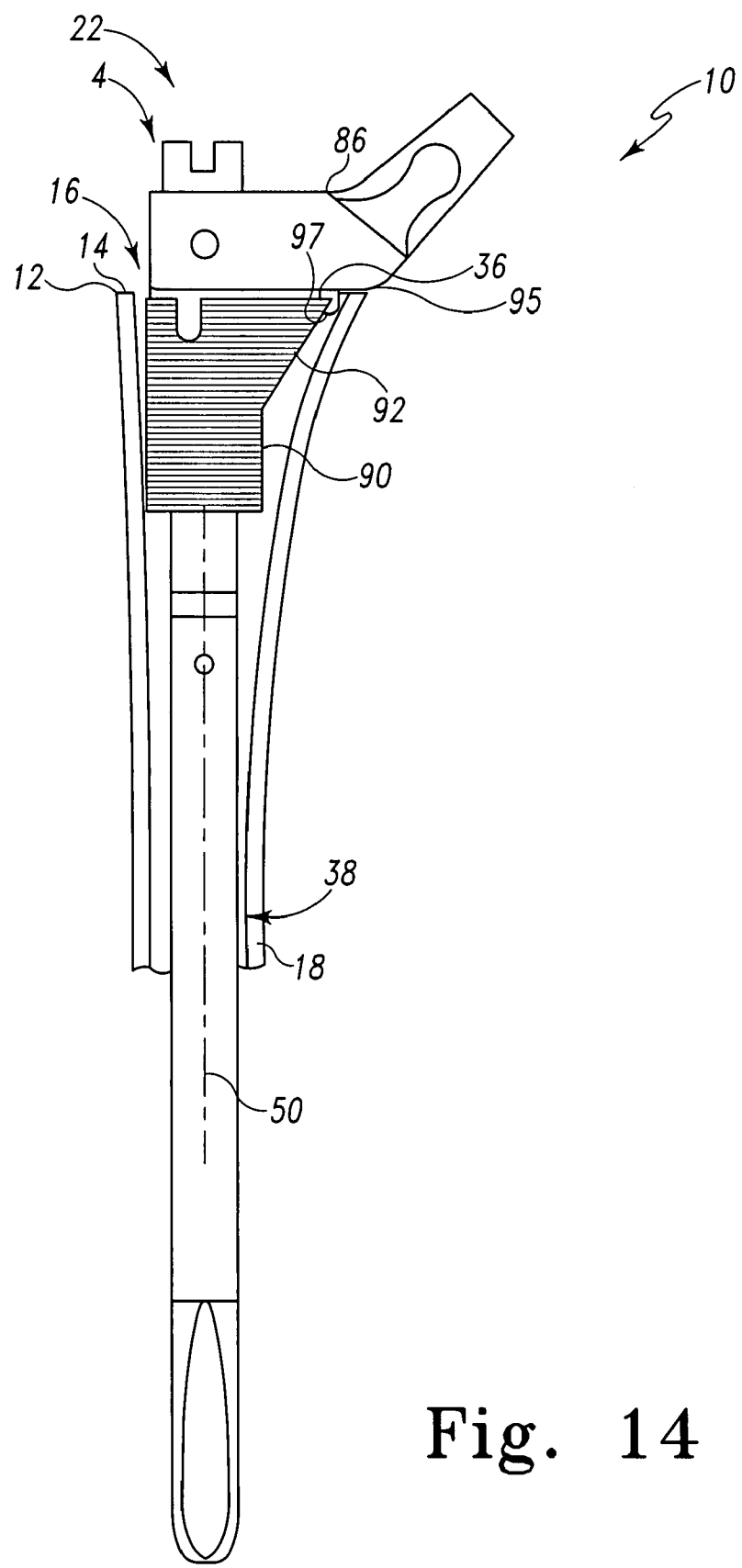
FIG. 14 is a plan view, partially in cross section, of the trial of the kit of FIG. 1, showing the trial in position in the reamed and resected femur.

Referring now to FIG. 14, the trial 22 is shown in position in the cavity 4 of the femur 18. The trial 22, as shown in FIG. 14, includes the distal stem 38 as well as neck trial 86. The neck trial 86 includes under surface 97 which is parallel to resected surface 14 of the femur 18. With the use of the kit and the calcar reamer the calcar bone 12 is removed from the resected surface 14 of the femur 18 underneath the distal face 97 of the neck trial 86. The resected surface 14 includes a recessed surface 95 which is distal from the resected surface 14 and provides for a space between the recessed face 95 and the under surface 97 of the neck trial 86 to assure that the neck trial 86 is properly seated to the distal stem 38 and that the neck trial 86 does not impinged upon resected surface 14 of the femur 18.

Figure 15:
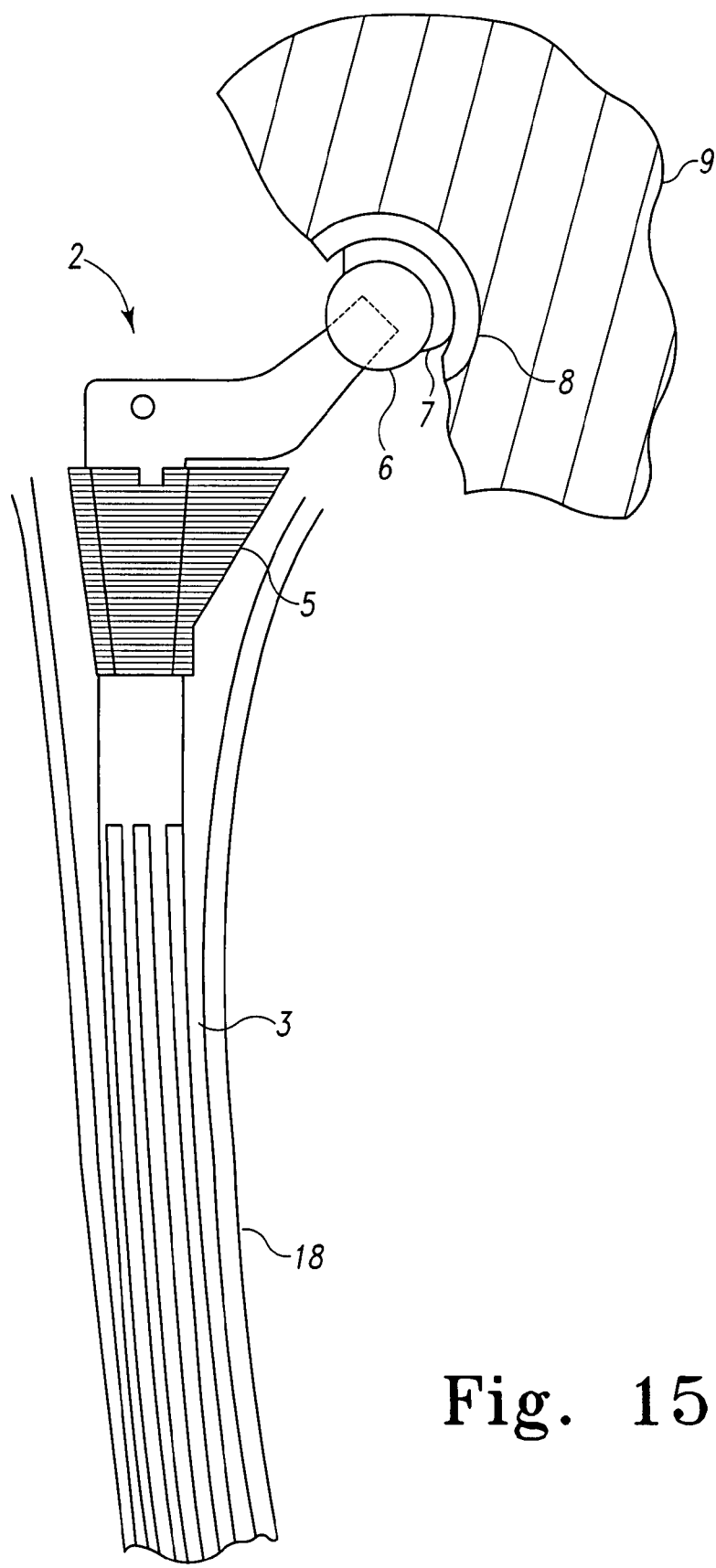
FIG. 15 is a plan view, partially in cross section, of the implant that corresponds to the trail of the kit of FIG. 1, showing the implant in position in the femur.

Referring now to FIG. 15, an implant 2 is shown to cooperate with the trial 22 of FIG. 14. The implant 2 includes a stem 3 and a sleeve 5 which slideably fits through the external periphery of stem 3. The stem 3 receives head 6. The head 6 articulates with bearing 7 supported by cup 8. The cup 8 is secured to acetabulum 9 thereby forming the implant 2.

Figure 16:
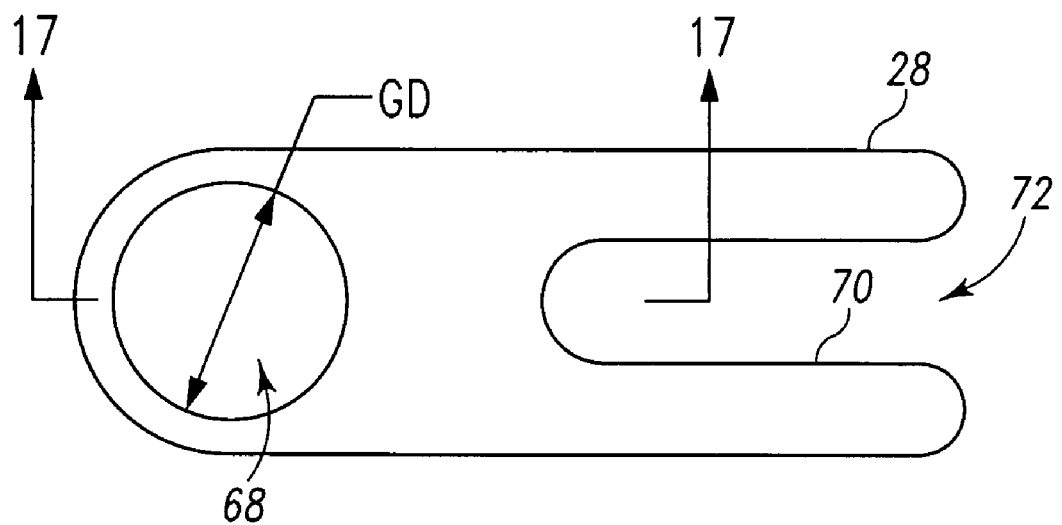
FIG. 16 is a top view of the guide of the kit of FIG. 1.
Figure 17:
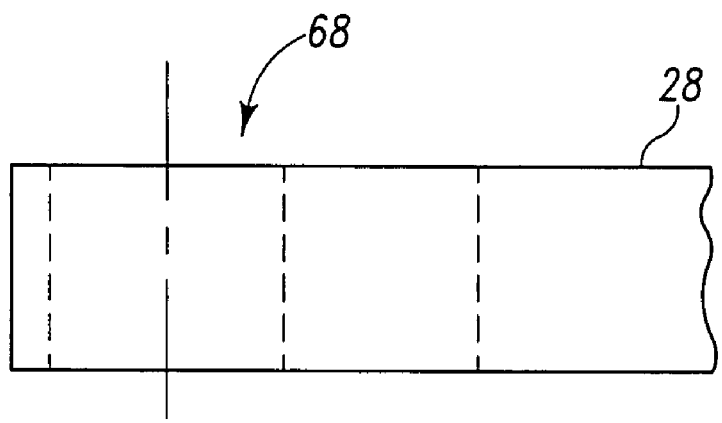
FIG. 17 is a cross sectional view of FIG. 16 along the line 17-17 in the direction of the arrows.

Referring now to FIGS. 16 and 17, the guide 28 is shown in greater detail. The guide 28 includes the guide opening 68 which is defined by diameter GD which matingly fits with shaft 74 of the reamer 30. The guide 28 further includes the slot 72 which is defined by the internal walls 70 of the guide 28.

Figure 18:
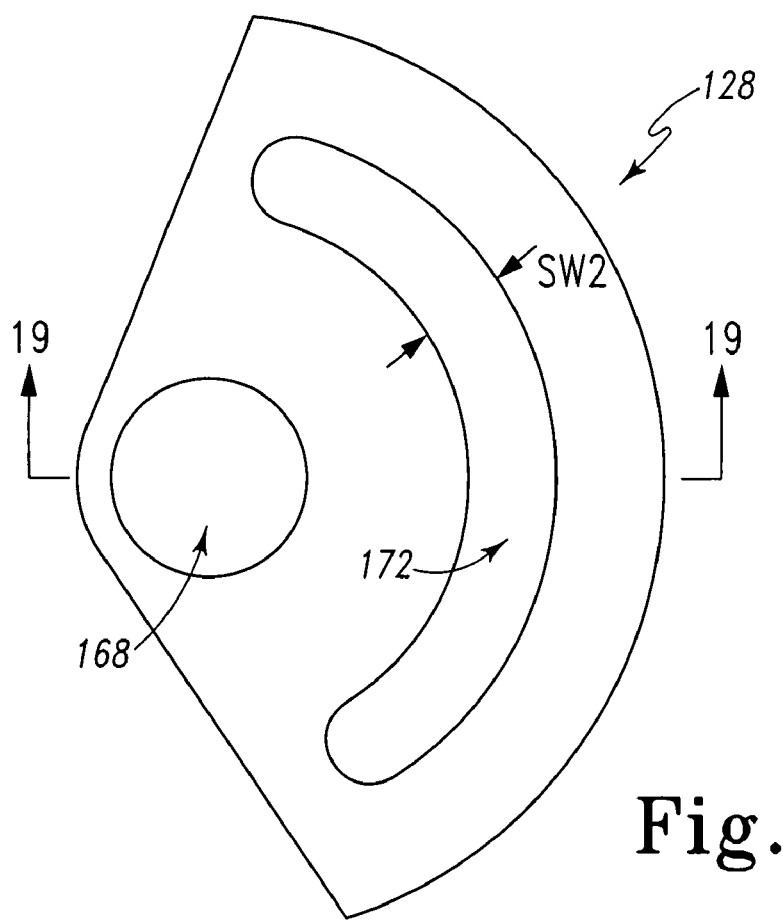
FIG. 18 is a top view of a guide with an arcuate slot to guide a calcar reamer according to another embodiment of the present invention.
Figure 19:
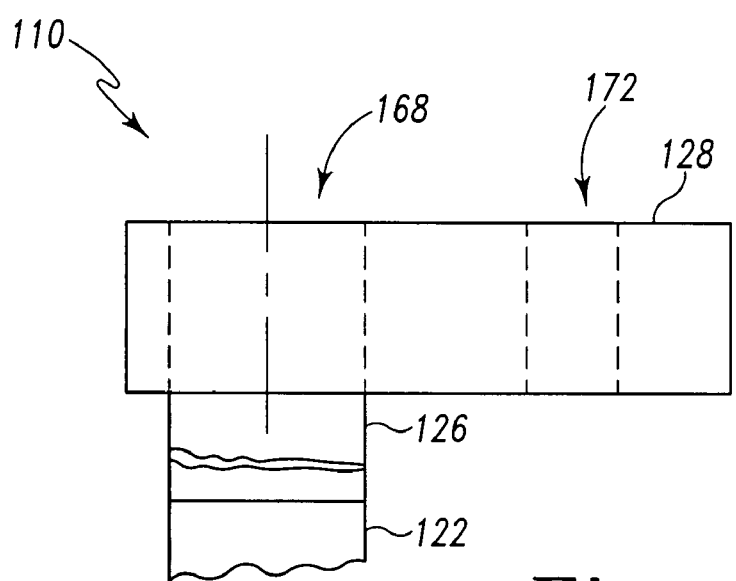
FIG. 19 is a cross sectional view of FIG. 18 along the line 19-19 in the direction of the arrows.

Referring now to FIGS. 18 and 19, another embodiment of the present invention is shown as kit 110. The kit 110 is similar to the kit 10, of FIG. 1, except that the kit 110 includes a guide 128 which is different than the guide 28 of the kit 10, of FIG. 1. The guide 128 includes a longitudinal opening 168 to pivotally rotate the guide 128 about column 126. It should be appreciated that the column 126 and trial 122 of the kit 110 may similar or identical to the column 26 and trial 22 of the kit 10, of FIG. 1. The guide 128 includes a slot 172 that is arcuate and defined by radius RG. The slot 172 has a slot width SW2 for mating movement with shaft 74 of the reamer 30.

Figure 20:
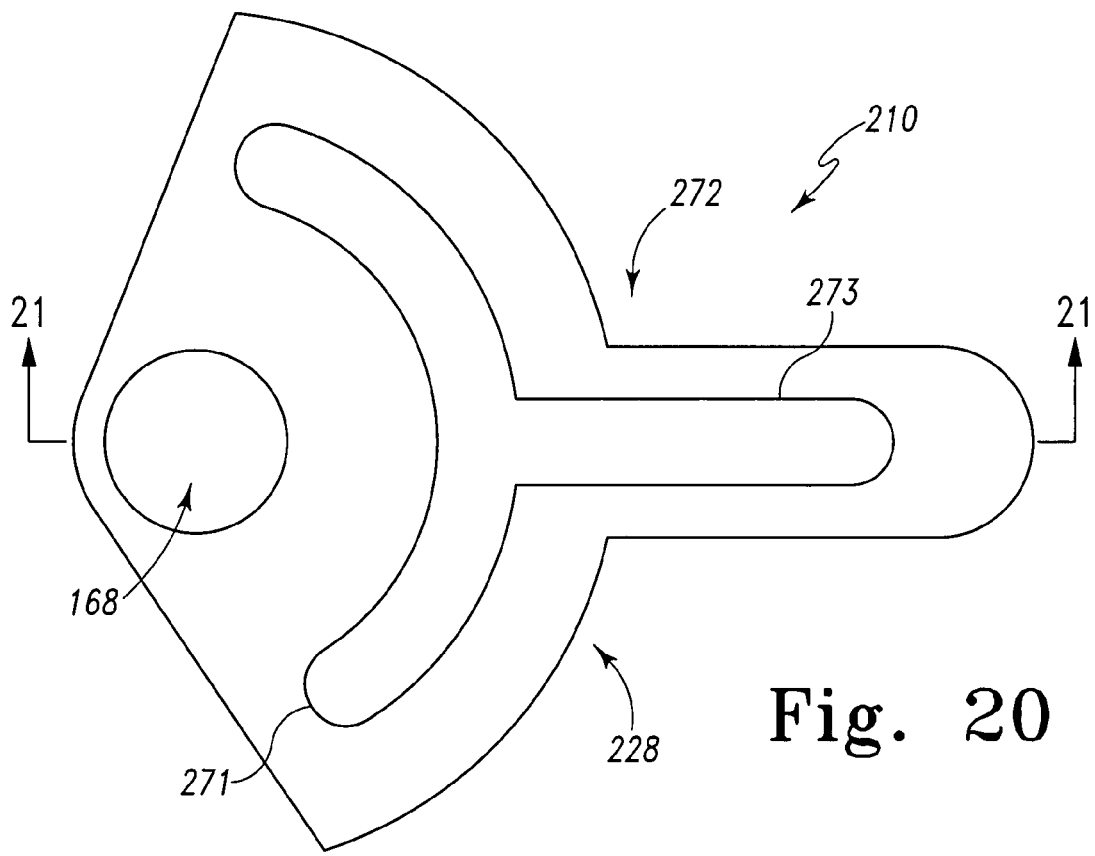
FIG. 20 is a top view of a guide with a T-shaped slot to guide a calcar reamer according to another embodiment of the present invention.
Figure 21:
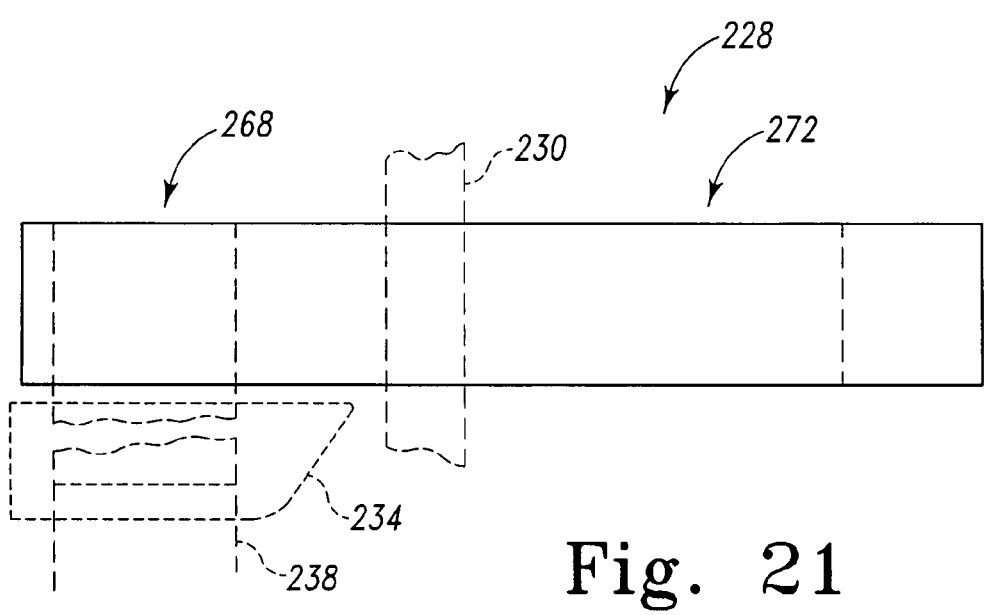
FIG. 21 is a cross sectional view of FIG. 20 along the line 21-21 in the direction of the arrows.

Referring now to FIGS. 20 and 21, another embodiment of the present invention is shown as kit 210. The kit 210 is similar to the kit 10 of FIG. 1. The kit 210 has a slot 272 including an arcuate, or circumferential, portion 271 and a radial portion 273 extending centrally from the circumferential portion 271 of the slot 272. The guide 228 includes a longitudinal opening 268 which provides rotational motion of the guide 228 about column 226. It should be appreciated that the column 226, calcar reamer 230, stem 238 and sleeve 234 may be the same as the column 26, calcar reamer 30, stem 38 and sleeve 34 of the kit 10 of FIG. 1.

Figure 22:
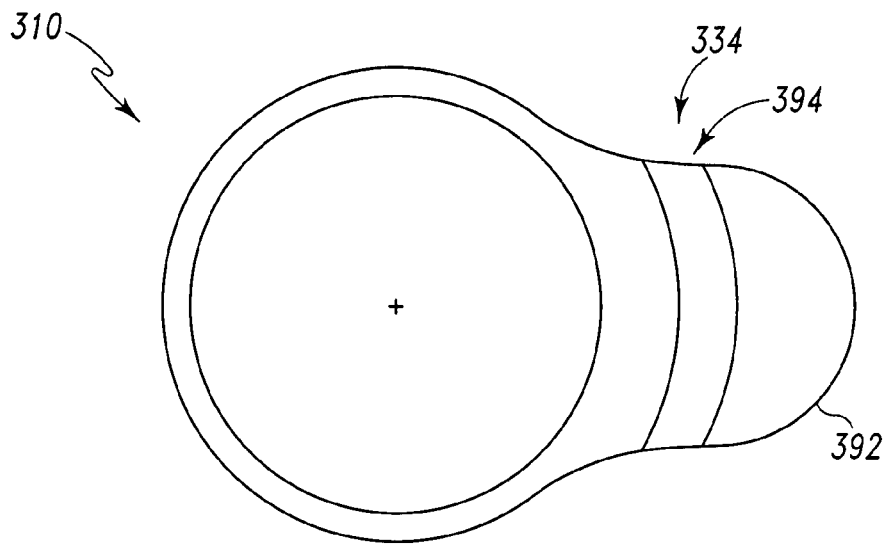
FIG. 22 is a top view of a trial sleeve with a transverse channel to guide a calcar reamer according to another embodiment of the present invention.
Figure 23:
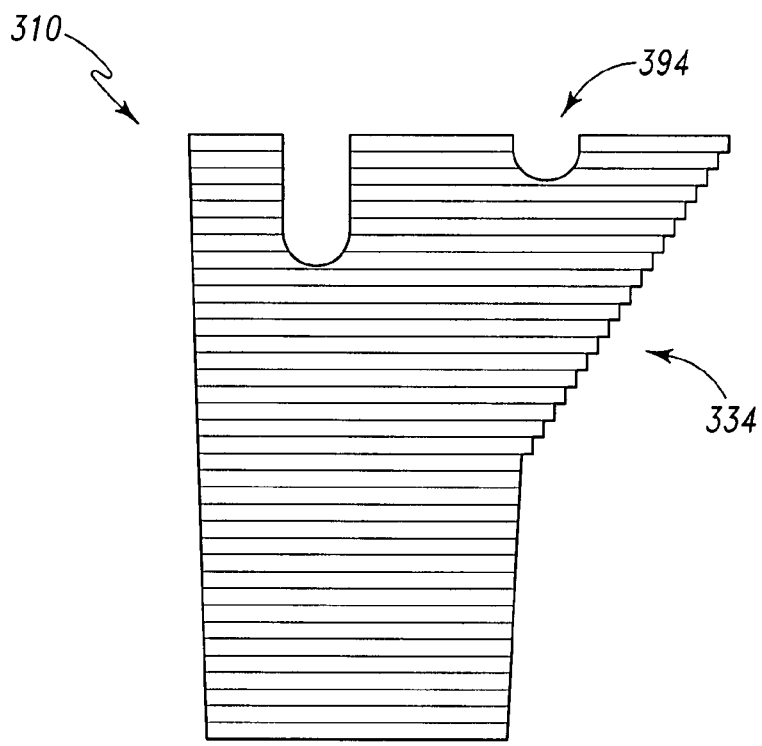
FIG. 23 is a plan view of the trial sleeve of FIG. 22.

Referring now to FIGS. 22 and 23, another embodiment of the present invention is shown as kit 310. The kit 310 is similar to the kit 10 of FIG. 1. The kit 310 includes a sleeve 334. The sleeve 334 of the kit 310 includes a channel 394 that is circumferential and extends across the width of spout 392 of the sleeve 334. It should be appreciated that the column 326, calcar reamer 330, and stem 338 may be the same as the column 26, calcar reamer 30, and stem 38 of the kit 10 of FIG. 1.

Figure 24:
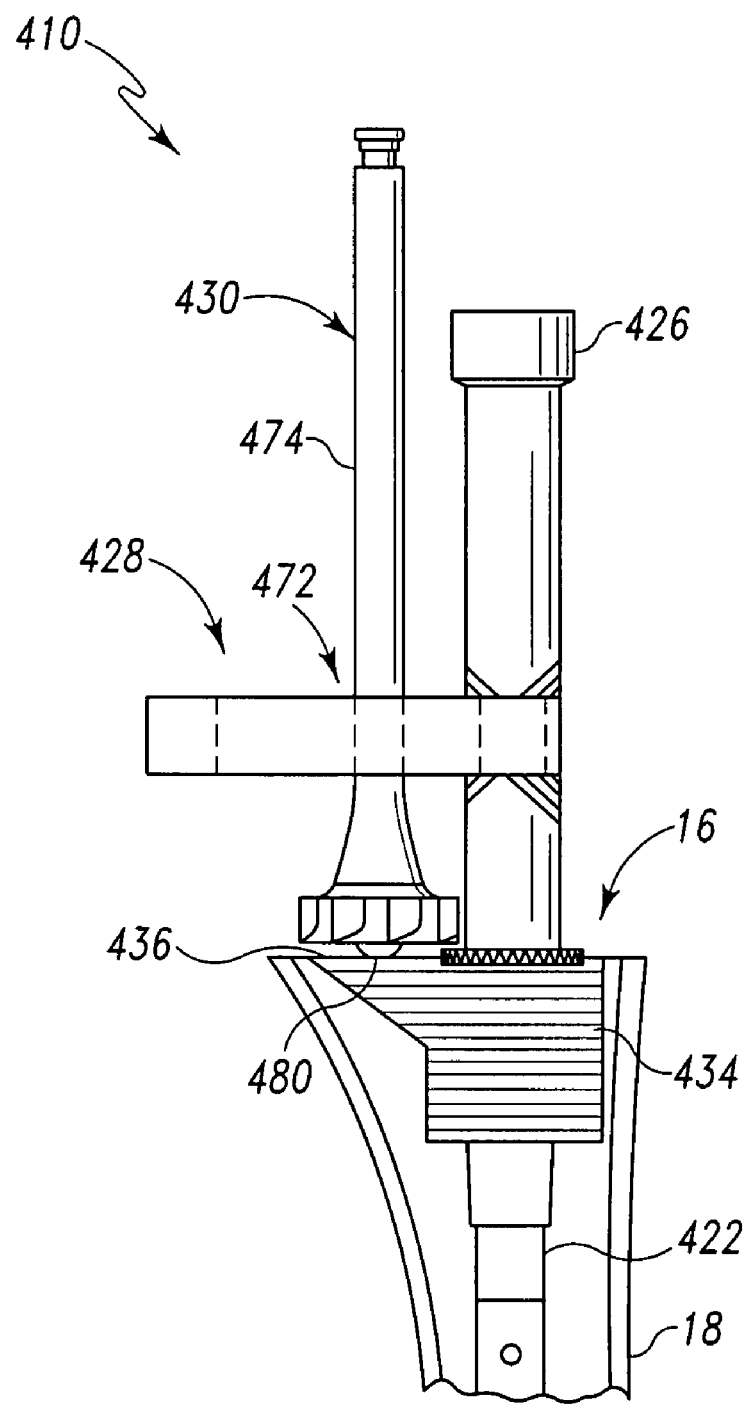
FIG. 24 is a plan view of a kit including a trial, column, guide and reamer having a guide that is fixedly secured to the column according to yet another embodiment of the present invention.
Figure 25:
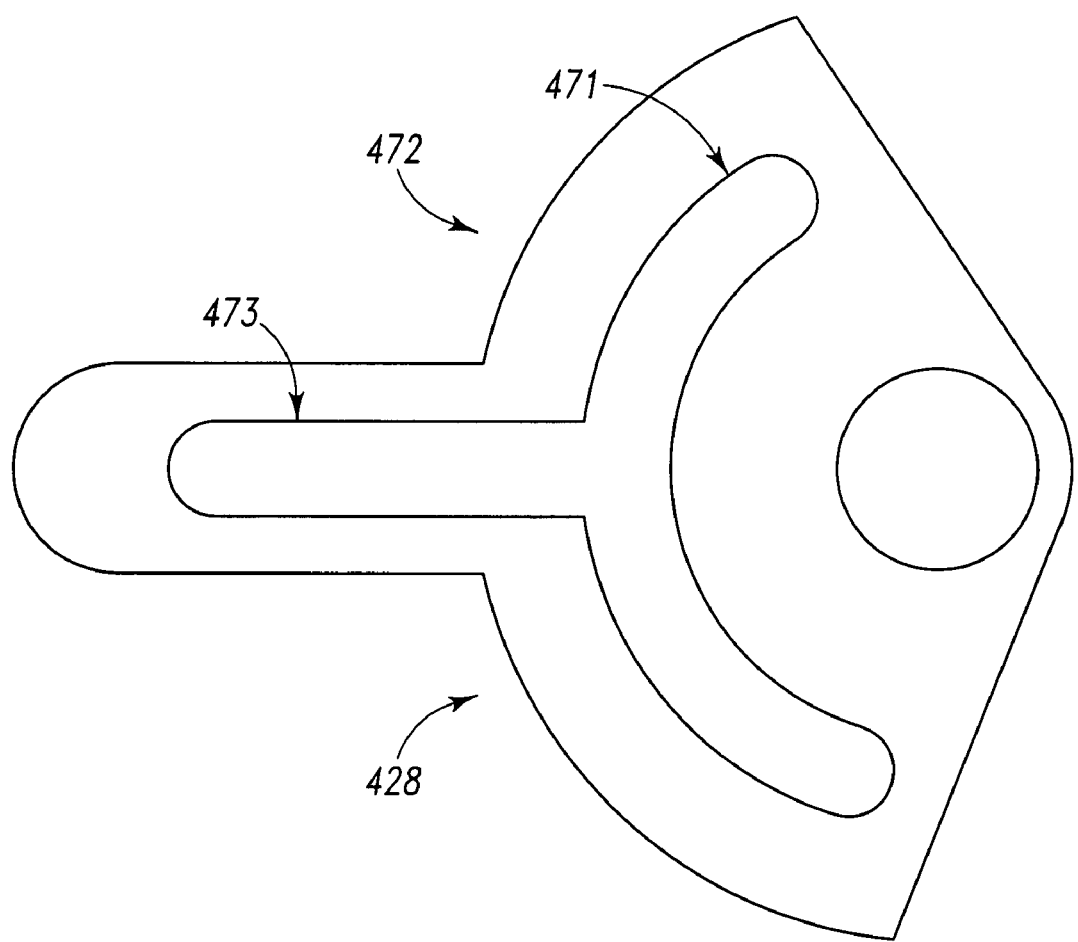
FIG. 25 is a top view of the guide of the kit of FIG. 24.

Referring now to FIGS. 24 and 25, yet another embodiment of the present invention is shown as kit 410. The kit 410 includes a guide 428 is rigidly secured to column 426. The guide 428 includes a T-shape slot 472 for receiving shaft 474 of reamer 430. The reamer 430 includes a pilot 480 for engagement with top face 436 of sleeve 434. The shaft 474 of reamer 430 is guided first along transverse portion 471 of the slot 472 and then along radial portion 473 of the slot 472 as the pilot is in contact with top face 436 of stem 434 to remove the calcar bone 12 from the femur 18.

Figure 26:
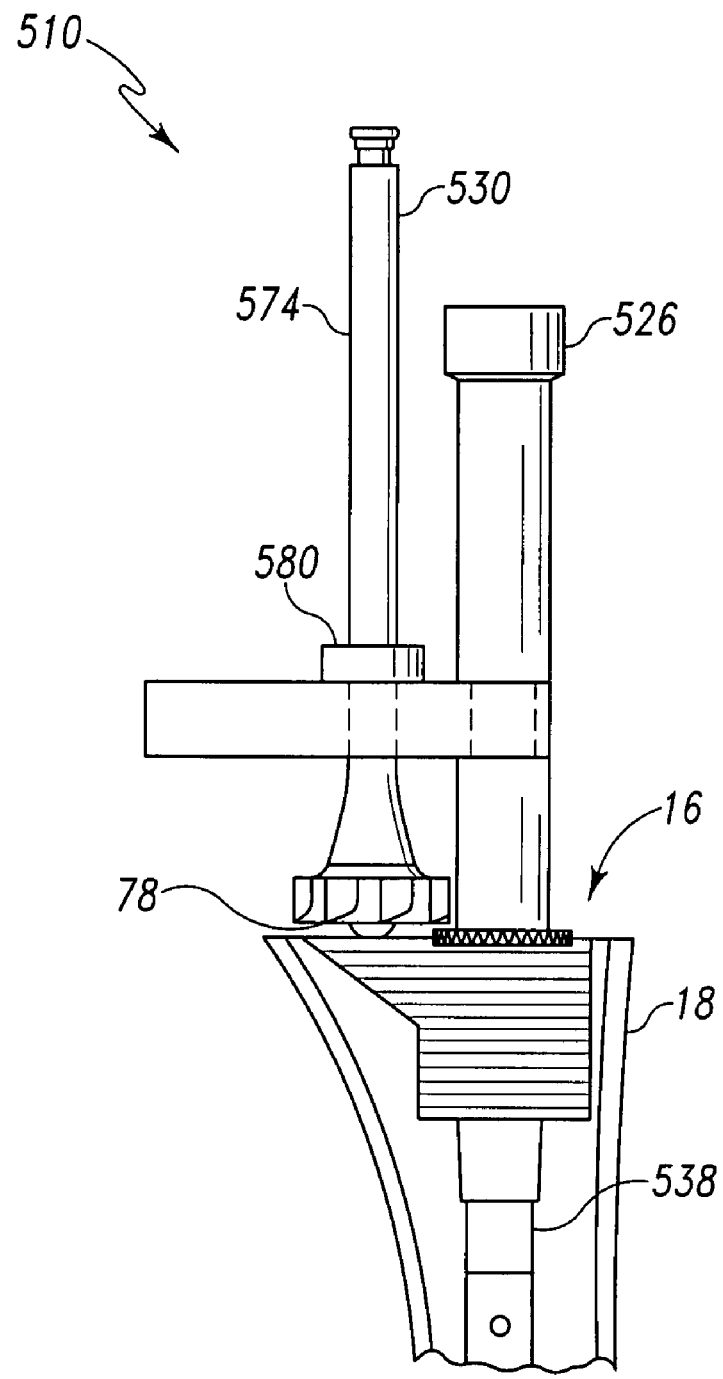
FIG. 26 is a plan view of a kit including a trial, column, guide and reamer having a reamer that is has a positive stop to cooperate with the column to set the reamer cutting height according to another embodiment of the present invention.
Figure 27:
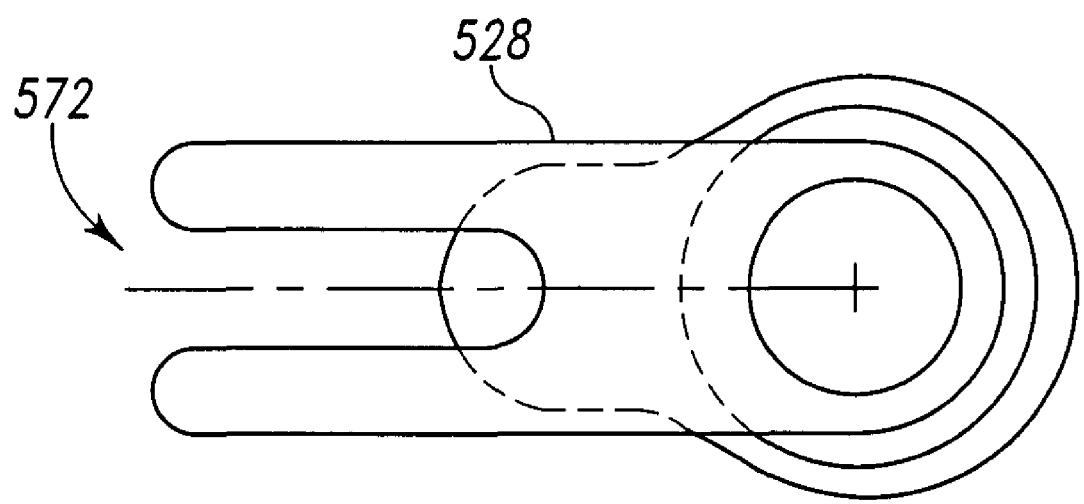
FIG. 27 is a top view of the guide of the kit of FIG. 26, shown over the sleeve.

Referring now to FIGS. 26 and 27, yet another embodiment of the present invention is shown as kit 510. The kit 510 is similar to the kit 10, of FIG. 1, except that the kit 510 includes a reamer 530 with a stop 580 which engages against the guide 428 to establish the depth of calcar bone 12 removed from femur 18. The guide 428 is rotatably fitted to column 536. The guide 528 includes a longitudinal slot 572 for cooperating with the shaft 574 of the reamer 530 to guide the reamer 530 along slot 572. The reamer 530 has a stop 580 to limit the movement of the cutting edge of the reamer 530 in a downward direction.

Figure 28:
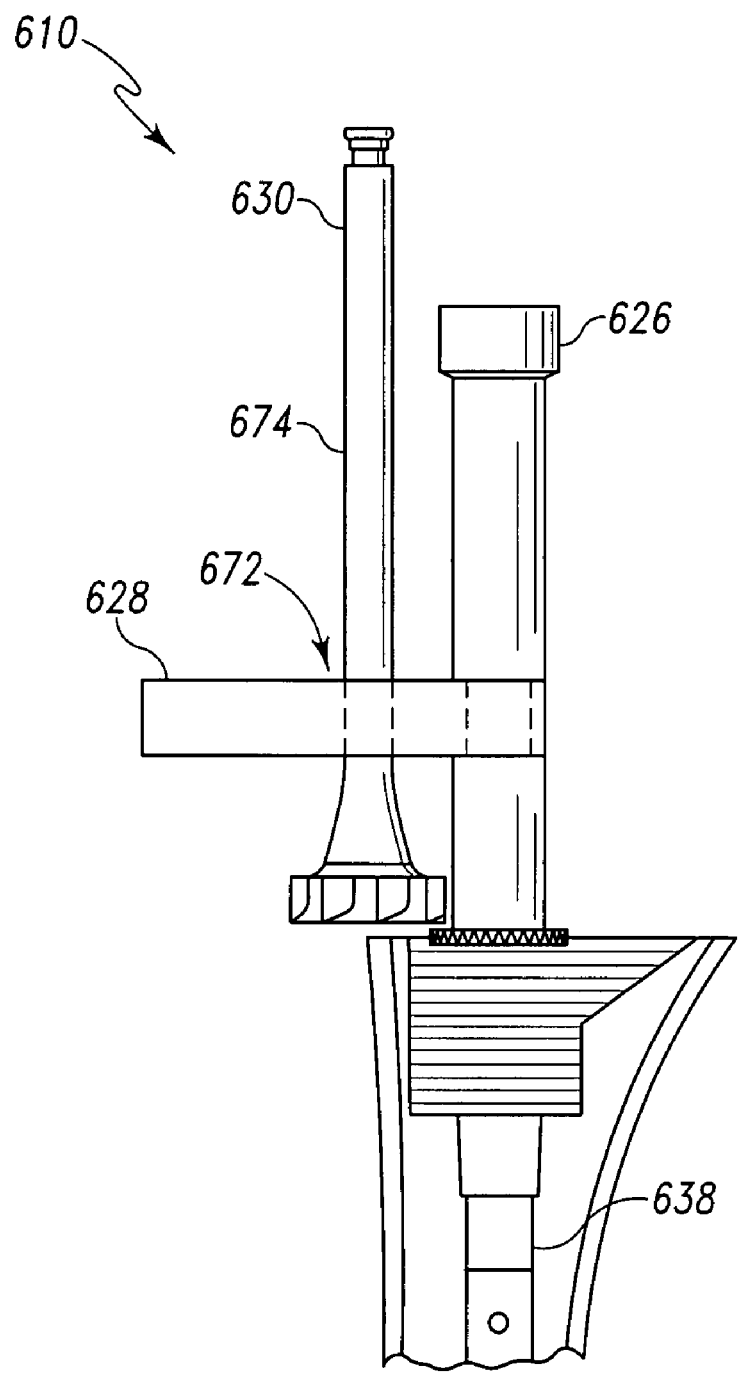
FIG. 28 is a plan view of a kit including a trial, column, guide and reamer having a having a guide that has a slot with an arcuate portion and a radial portion according to another embodiment of the present invention.
Figure 29:
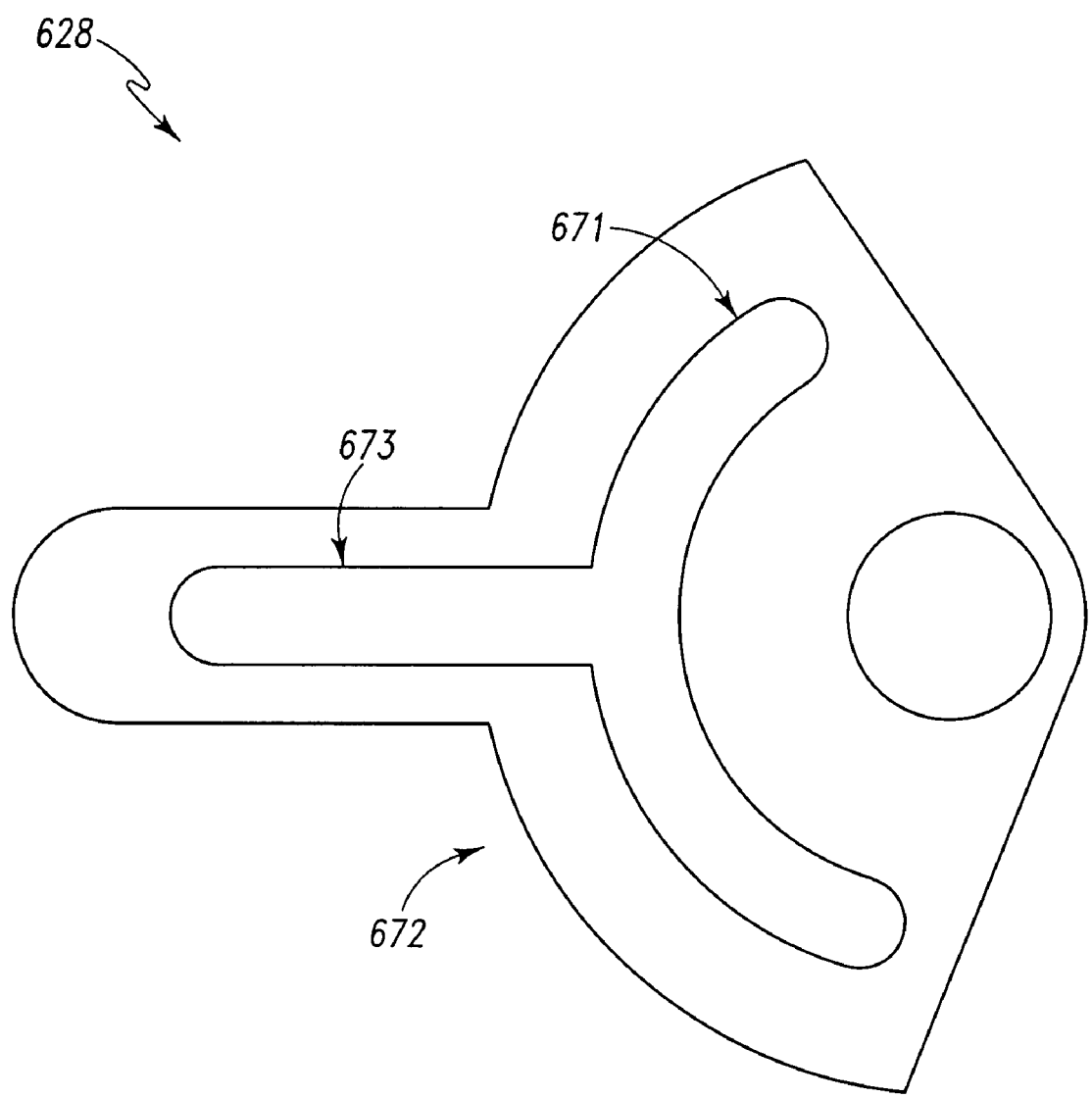
FIG. 29 is a top view of the guide of the kit of FIG. 28.

Referring now to FIGS. 28 and 29, yet another embodiment of the present invention is shown as kit 610. The kit 610 includes a guide 628 which is rigidly secured to the column 626. The guide 628 includes a slot 672 which includes an arcuate portion 671 and a radial portion 673. The slot 672 is matingly sized to receive shaft 674 of the reamer 630 to guide the reamer 630. The reamer 630 includes a stop 680 to control the depth of the calcar bone cut of the reamer 630.

Figure 30:
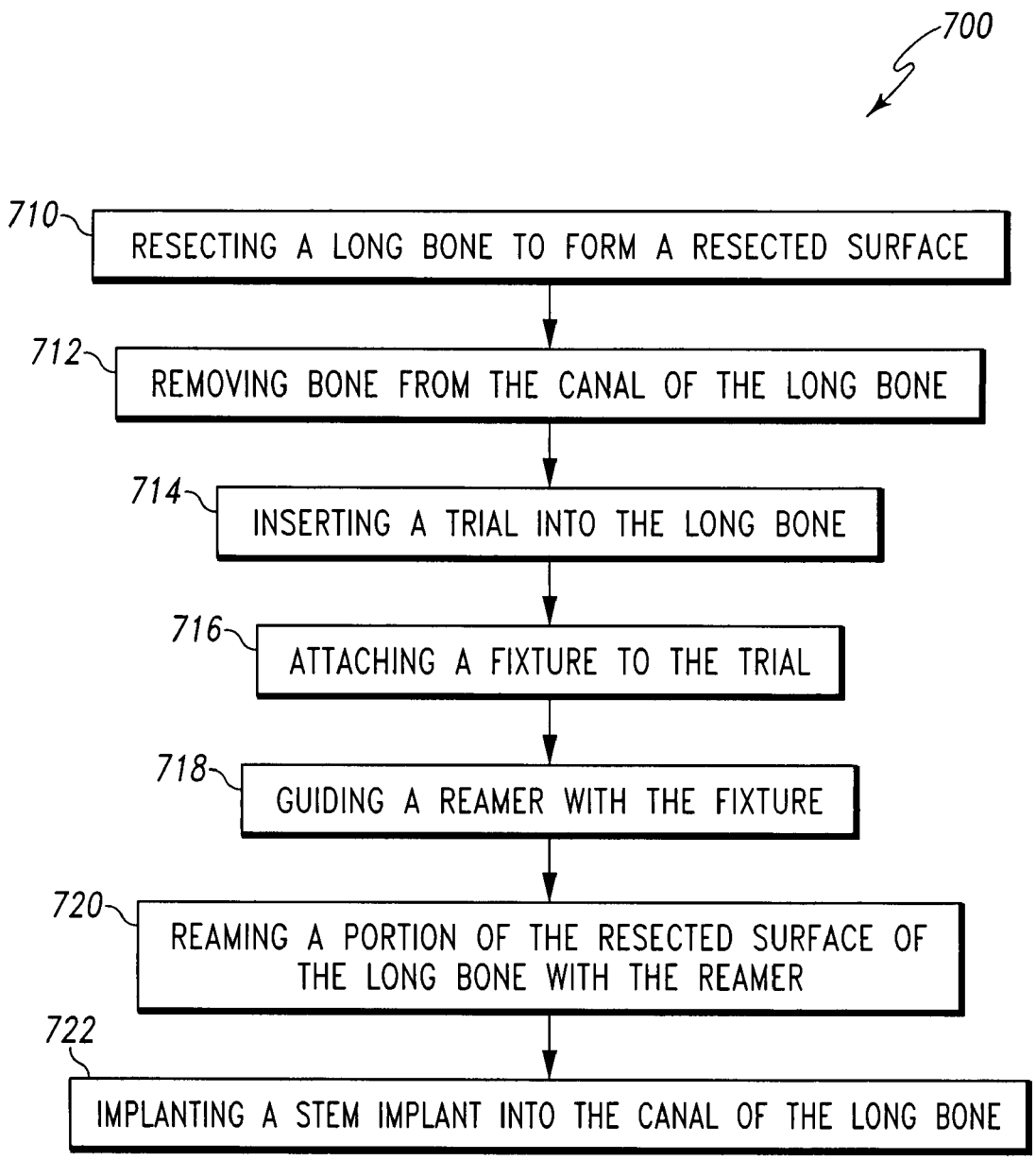
FIG. 30 is a process flow chart for a surgical procedure for performing an arthroplasty according to another embodiment of the present invention.

Referring now to FIG. 30, yet another embodiment of the present invention is shown as surgical procedure or method 700. The method includes a first step 710 of resecting a long bone to form a resected surface and a second step 712 of removing bone from the canal of the long bone. The method also includes a third step 714 of inserting a trial into the long bone and a fourth step 716 of attaching a fixture to the trial. The method further includes a fifth step 718 of guiding a reamer with a fixture and a sixth step 720 of reaming a portion of the resected surface of the long bone with the reamer. The method further includes a seventh step 722 of implanting a stem implant into the canal of the long bone.

Although the present invention and its advantages have been described in detail, it should be understood that various changes, substitutions, and alterations can be made therein without departing from the spirit and scope of the present invention, as defined by the appended claims.

We claim:

1. A kit for removing calcar bone from a resected face around a bone canal of a long bone, said kit, comprising:
    a calcar reamer for removing calcar bone from the resected face around the bone canal of the long bone;
    a trial for insertion into the bone canal of the long bone, said trial including a cone with a proximal surface;
    an arcuate channel in the proximal surface configured to stop movement of the calcar reamer along a longitudinal axis of the long bone and configured to guide movement of the calcar reamer along an arcuate path orthogonal to the long bone longitudinal axis;
    a fixture including a connector for connecting said fixture to said trial and a guide for guiding the calcar reamer along the resected face; and
    an implant for insertion into the bone canal of the long bone.

2. The kit of claim 1, wherein said fixture is threadably connected to said trial.

3. The kit of claim 1, wherein said guide defines a wall thereof, the wall defining a slot for guiding the calcar reamer along a straight path defined by the channel and orthogonal to the long bone longitudinal axis.

4. The kit of claim 1, wherein said fixture comprises:
    a column, said column defining a columnar longitudinal axis and an external periphery thereof, said column being threadably attachable to said trial; and
    an arm extending outwardly from and connected to the external periphery of said column, said arm defines a wall thereof, the wall defining a slot for guiding the calcar reamer along a straight path defined by the channel and orthogonal to the long bone longitudinal axis.

5. The kit of claim 4, wherein said arm is rotatably connected to said column for rotation about the columnar longitudinal axis.

6. The kit of claim 1, wherein said fixture comprises:
a column, said column defining a columnar longitudinal axis and a cylindrical external periphery thereof, said column having an internal wall defining a cavity extending inwardly from a first end of said column the internal wall being threaded to mate with an external fastener on said trial; and
an arm extending outwardly from and rigidly connected to the external periphery of said column, said arm defines a wall thereof, the wall defining a slot for guiding the calcar reamer along a straight path defined by the channel and orthogonal to the long bone longitudinal axis.

7. The kit of claim 1, wherein said reamer comprises:
a shaft portion;
an end mill including a plurality of cutting edges extending from a first end of said shaft portion;
a pilot extending downwardly from the end mill and configured to fit at least partially within the channel; and
a connector extending from a second end of said shaft portion, opposed to the first end.

8. A kit for removing calcar bone from a resected face around a bone canal of a long bone, said kit, comprising:
a trial including (i) a stem for insertion into the bone canal of the long bone, the stem defining a longitudinal axis, and (ii) a cone extending from a proximal end portion of said stem, said cone including a proximal surface thereof, the proximal surface defining an arcuate channel;
a fixture including a connector for connecting said fixture to said trial and a guide; and
a calcar reamer for removing calcar bone from the resected face around the bone canal of the long bone, said reamer including a feature for cooperation with the guide of said fixture and configured for guidance by the channel along an arcuate path orthogonal to the longitudinal axis while cooperating with the guide.

9. The kit of claim 8, wherein said fixture is threadably connected to said trial.

10. The kit of claim 8, wherein said guide defines a wall thereof, the wall defining a slot for guiding the calcar reamer.

11. The kit of claim 8, wherein said fixture comprises:
a column, said column defining an external periphery thereof, said column being threadably attachable to said trial; and
an arm extending outwardly from and connected to the external periphery of said column, said arm defines a wall thereof, the wall defining a slot for guiding the calcar reamer.

12. The kit of claim 11, wherein said arm is rotatably connected to said column for rotation about the longitudinal axis.

13. The kit of claim 8, wherein the feature of said reamer for cooperation with the guide of said fixture includes a stop for limiting axial movement of said reamer.

14. The kit of claim 8, wherein said fixture comprises:
a column, said column defining a cylindrical external periphery thereof, said column having an internal wall defining a cavity extending inwardly from a first end of said column the internal wall being threaded to mate with an external fastener on said trial; and
an arm extending outwardly from and rigidly connected to the external periphery of said column, said arm defines a wall thereof, the wall defining a slot for guiding the calcar reamer along a straight path defined by the channel and orthogonal to the longitudinal axis.

15. The kit of claim 8, wherein said reamer comprises:
a shaft portion defining an external periphery thereof;
an end mill including a plurality of cutting edges extending from a first end of said shaft portion; and
a connector extending from a second end of said shaft portion, opposed to the first end.

16. The kit of claim 15, wherein the end mill of said reamer includes a pilot extending downwardly from the end mill and configured to fit at least partially within the channel.

17. An instrument assembly for use with an orthopaedic implant trial for removing calcar bone from a resected face around a bone canal of a long bone, said instrument assembly, comprising:
a fixture including a connector for connecting said fixture to the trial and a guide; and
a calcar reamer for removing calcar bone from the resected face around the bone canal of the long bone, said reamer including
a feature for cooperation with the guide of said fixture,
a shaft portion defining a longitudinal axis, an end mill located at a first end portion of said shaft portion, and
an arcuate pilot extending downwardly from the end mill and configured to come into contact with an arcuate channel of the trial as the end mill moves along the longitudinal axis.

18. A trial for use with a reamer having an arcuate pilot on a proximal portion thereof, the reamer for removing calcar bone from a resected face around a bone canal of a long bone, said trial comprising:
a body portion including a stem for insertion into the bone canal of the long bone, the stem defining a longitudinal axis of said body portion; and
a cone extending from the proximal end of said body portion, said cone including a proximal surface thereof, the proximal surface being generally normal to the longitudinal axis of said body portion, the proximal surface defining an arcuate channel extending along a path therein, the channel adapted to mate with an arcuate pilot of the reamer.

19. A method for performing joint arthroplasty comprising:
resecting a long bone to form a resected surface; removing bone from the canal of the long bone;
inserting a trial into the canal of the long bone;
attaching a fixture defining a longitudinal axis to the trial such that the longitudinal axis is substantially perpendicular to the resected surface; guiding a reamer with the fixture; moving the reamer along the longitudinal axis into contact with a surface of the trial;
guiding the reamer in a direction toward the canal along the resected surface with a the surface of the trial;
reaming a portion of the resected surface of the long bone with the reamer as the reamer is guided toward the canal; and implanting a stem implant into the canal of the long bone.

* * * * *